US012609183B2

(12) United States Patent
Dutton et al.

(10) Patent No.: US 12,609,183 B2
(45) Date of Patent: Apr. 21, 2026

(54) SPACIO-TEMPORAL DETERMINATION OF POLYPEPTIDE STRUCTURE

(71) Applicant: PEPTONE, LTD., London (GB)

(72) Inventors: Oliver Dutton, Yorkshire (GB); Carlo Fisicaro, Lugano (CH); Matthew Michael Heberling, Vigo (ES); Louie Derek Henderson, London (GB); Istvan Redl, London (GB); Kamil Tamiola, Aosta (IT)

(73) Assignee: Peptone, LTD., London (GB)

( * ) Notice: Subject to any disclaimer, the term of this patent is extended or adjusted under 35 U.S.C. 154(b) by 39 days.

(21) Appl. No.: 18/598,694

(22) Filed: Mar. 7, 2024

(65) Prior Publication Data

US 2024/0221864 A1     Jul. 4, 2024

Related U.S. Application Data

(63) Continuation of application No. 18/513,867, filed on Nov. 20, 2023, which is a continuation of application No. PCT/IB2022/054705, filed on May 19, 2022.

(30) Foreign Application Priority Data

May 21, 2021    (EP) ..................................... 21382464

(51) Int. Cl.
| | |
|---|---|
| *G16B 15/30* | (2019.01) |
| *C07K 14/735* | (2006.01) |
| *G16B 30/10* | (2019.01) |
| *G16B 35/00* | (2019.01) |
| *G16B 40/00* | (2019.01) |
| *G16B 40/20* | (2019.01) |

(52) U.S. Cl.
CPC ........ *G16B 15/30* (2019.02); *C07K 14/70535* (2013.01); *G16B 30/10* (2019.02); *G16B 35/00* (2019.02); *G16B 40/00* (2019.02); *G16B 40/20* (2019.02)

(58) Field of Classification Search
None
See application file for complete search history.

(56) References Cited

U.S. PATENT DOCUMENTS

| | | |
|---|---|---|
| 10,706,955 B2 | 7/2020 | Bremel |
| 10,934,302 B1 | 3/2021 | Taylor |
| 2010/0233176 A1 | 9/2010 | Cashman |
| 2020/0020415 A1 | 1/2020 | Sarmiento |
| 2021/0134389 A1 | 5/2021 | Wu |

FOREIGN PATENT DOCUMENTS

| | | |
|---|---|---|
| WO | 2020242766 A1 | 12/2020 |

OTHER PUBLICATIONS

Soria-Guerra, Ruth E et al. "An Overview of Bioinformatics Tools for Epitope Prediction: Implications on Vaccine Development." Journal of biomedical informatics 53 (2015): 405-414. Web. (Year: 2016).*

Saadi, Mahdiye, Ahmad Karkhah, and Hamid Reza Nouri. "Development of a Multi-Epitope Peptide Vaccine Inducing Robust T Cell Responses against Brucellosis Using Immunoinformatics Based Approaches." Infection, genetics and evolution 51 (2017): 227-234 . Web. (Year: 2017).*

Fleri, Ward et al. "The Immune Epitope Database and Analysis Resource in Epitope Discovery and Synthetic Vaccine Design." Frontiers in immunology 8 (2017): 278-278. Web. (Year: 2017).*

Dall'Antonia, Fabio et al. "Structure of Allergens and Structure Based Epitope Predictions." Methods (San Diego, Calif.) 66.1 (2014): 3-21. Web. (Year: 2014).*

Naveed, Muhammad et al. "Design of a Novel Multiple Epitope-Based Vaccine: An Immunoinformatics Approach to Combat SARS-CoV-2 Strains." Journal of infection and public health 14.7 (2021): 938-946. Web. (Year: 2021).*

Hajighahramani, Nasim et al. "Immunoinformatics Analysis and in Silico Designing of a Novel Multi-Epitope Peptide Vaccine against *Staphylococcus aureus*." Infection, genetics and evolution 48 (2017): 83-94. Web. (Year: 2017).*

Jakhar, Renu, and S. K Gakhar. "An Immunoinformatics Study to Predict Epitopes in the Envelope Protein of SARS-CoV-2." The Canadian journal of infectious diseases & medical microbiology 2020 (2020): 1-14. Web (Year: 2020).*

Nezafat, Navid et al. "A Novel Multi-Epitope Peptide Vaccine against Cancer: An in Silico Approach." Journal of theoretical biology 349 (2014): 121-134. Web. (Year: 2014).*

Ansari et al., (2010), 'Identification of conformational B-cell Epitopes in an antigen from its primary sequence', Immunome Research , vol. 6, p. 1-9.

Bai, Y., et al. "Unsupervised inductive graph-level representation learning via graph-graph proximity." arXiv preprint arXiv:1904. 01098 (2019).

Bepler, T., and Berger, B. "Learning protein sequence embeddings using information from structure." arXiv preprint arXiv:1902.08661 (2019).

Best et al., (2013) 'Native contacts determine protein folding mechanisms in atomistic simulations', Proceedings of the National Academy of Sciences , 110(44), pp. 17874-17879.

(Continued)

*Primary Examiner* — Anna Skibinsky
*Assistant Examiner* — Josep Pulliam
(74) *Attorney, Agent, or Firm* — Greenberg Traurig, LLP

(57) ABSTRACT

Disclosed herein are methods of in silico generation of polypeptide structures using time-based data generated from molecular dynamics simulations. Also disclosed herein are methods of predicting an epitope or binding surface of a polypeptide using in silico methods. Also disclosed herein are compositions containing polypeptide therapeutics designed to bind to a predicted epitope structure of a polypeptide, as well as methods of treating a subject by administering to the subject compositions containing the same.

17 Claims, 11 Drawing Sheets

Specification includes a Sequence Listing.

(56)     References Cited

OTHER PUBLICATIONS

Bioinformatics Web Servers—University of Reading (no date). Available at: https://www.reading.ac.uk/bioinf/DISOclust/ (Accessed: Aug. 11, 2022).

Bornot et al., (2011) 'Predicting protein flexibility through the prediction of local structures', Proteins , vol. 79, No. 3, pp. 839-852.

Current Release Statistics < Uniprot < EMBL-EBI (no date). Available at: https://www.ebi.ac.uk/uniprot/TrEMBLstats (Accessed: Aug. 11, 2022).

Deng et al., (2019) 'MADOKA: an ultra-fast approach for large-scale protein structure similarity searching', BMC Bioinformatics , vol. 20, S19, p. 1-10.

Green et al., (2019) 'Proteome-scale discovery of protein interactions with residue-level resolution using sequence coevolution', bioRxiv , p. 1-27.

Groups Analysis: zscores—CASP12, 2016, Available at: https://predictioncenter.org/casp12/zscores_final.cgi (Accessed: Aug. 11, 2022).

Groups Analysis: zscores—CASP13 (no date). Available at: https://predictioncenter.org/casp13/zscores_final.cgi (Accessed: Aug. 11, 2022).

Hooshmand et al., (2020) 'Prediction of B cell and T-helper cell epitopes candidates of bovine leukaemia virus (BLV) by in silico approach', Veterinary Medicine and Science , 6(4), pp. 730-739.

Hopf et al., (2019) 'The EVcouplings Python framework for coevolutionary sequence analysis', Bioinformatics , vol. 35, No. 9, pp. 1582-1584.

International Search Report and Written Opinion for PCT/IB2022/054705 mailed Oct. 10, 2022.

Jespersen et al., (2017) 'BepiPred-2.0: improving sequence-based B-cell epitope prediction using conformational epitopes', Nucleic Acids Research , 45(W1), pp. W24-W29.

Kazemi et al., 2020, 'Representation Learning for Dynamic Graphs: A Survey', Journal of Machine Learning Research, vol. 21, p. 1-73.

Lin et al., (2013) 'Prediction of B-cell epitopes using evolutionary information and propensity scales', BMC Bioinformatics , vol. 14, No. 2, S10, p. 1-9.

Mahdavi, S., et al. "dynnode2vec: Scalable dynamic network embedding." 2018 IEEE international conference on big data (Big Data). IEEE, 2018.

Manavalan et al., (2018), 'iBCE-EL: A New Ensemble Learning Framework for Improved Linear B-Cell Epitope Prediction', Frontiers in Immunology , vol. 9, Article 1695, p. 1-11.

Meszaros et al., (2018) 'IUPred2A: context-dependent prediction of protein disorder as a function of redox state and protein binding', Nucleic Acids Research , 46(W1), pp. W329-W337.

Miotto, M., et al. "Insights on protein thermal stability: a graph representation of molecular interactions." Bioinformatics 35.15 (2019): 2569-2577.

Mitternacht, (2016) 'FreeSASA: An open source C library for solvent accessible surface area calculations', F1000Research , vol. 5, p. 1-10.

Mohan et al., (2020) In silico prediction of b-cell epitopes of dengue virus—A reverse vaccinology approach , Journal of Applied Pharmaceutical Scienc, vol. 10, No. 10, p. 077-085.

Nguyen et al., 2018, 'Continuous-Time Dynamic Network Embeddings', Track: Third International Workshop on Learning, p. 969-976.

Parvizpour et al. (2020) 'Epitope-based vaccine design: a comprehensive overview of bioinformatics approaches', Drug Discovery Today , 25(6), pp. 1034-1042.

Pavlovic et al., (2014) 'Epitope distribution in ordered and disordered protein regions. Part B—Ordered regions and disordered binding sites are targets of T- and B-cell immunity', Journal of Immunological Methods , 407, pp. 1-18.

Peptone Ltd., "Peptone: unlocking the therapeutic potential of intrinsically disordered proteins" Sep. 2022, Nature Biopharmadealmakers, vol. 16, Issue 3, Sep. 2022, B36, 1 page, www.nature.com/biopharmdeal.

Pfaff, T., et al., 'Learning Mesh-Based Simulation with Graph Networks', Published Conference Paper ICLR 2021, p. 1-18.

Potocnakova et al., (2016) An Introduction to B-Cell Epitope Mapping and In Silico Epitope Prediction , Journal of Immunology Research, vol. 216, Article 6760830, p. 1-11.

Protein BLAST: search protein databases using a protein query. Available at: https://blast.ncbi.nlm.nih.gov/Blast.cgi?PAGE= Proteins (Aug. 11, 2022).

Rahman et al., (2016) 'Inadequate Reference Datasets Biased toward Short Non-epitopes Confound B-cell Epitope Prediction', The Journal of Biological Chemistry , 291(28), pp. 14585-14599.

RCSB Protein Data Bank: Homepage . Available at: https://www.rcsb.org/ (Accessed: Aug. 11, 2022).

Rockafellar, R.T., and Wets, R.J.B. Variational analysis. vol. 317., p. 117, Springer Science & Business Media, 2009, ISBN 3-540-62772-3.

Saha et al., (2004) 'BcePred: Prediction of Continuous B-Cell Epitopes in Antigenic Sequences Using Physico-chemical Properties', in Nicosia, G. et al. (eds) Artificial Immune Systems . Berlin, Heidelberg: Springer (Lecture Notes in Computer Science), pp. 197-204.

Schrodinger/pymol-open-source (2021). Schrödinger, Inc. Available at: https://github.com/schrodinger/pymol-open-source (Aug. 11, 2022).

The Cost of Sequencing a Human Genome, Genome.gov . Available at: https://www.genome.gov/about-genomics/fact-sheets/Sequencing-Human-Genome-cost (Aug. 11, 2022).

Tsuchiya et al., 2020, Neural networks for protein structure and function prediction and dynamic analysis; Biophysical Reviews, vol. 12, p. 569-573.

Yang et al., (2020) 'Improved protein structure prediction using predicted interresidue orientations', Proceedings of the National Academy of Sciences , vol. 117, No. 3, pp. 1496-1503.

Glielmo, Aldo, et al. "Unsupervised learning methods for molecular simulation data." Chemical Reviews 121.16 (2021): 9722-9758.

Gong, Linchen, Xin Zhou, and Zhongcan Ouyang. "Systematically constructing kinetic transition network in polypeptide from top to down: trajectory mapping." Plos one 10.5 (2015): e0125932.

Russo, Anna, et al. "In silico generation of peptides by replica exchange Monte Carlo: Docking-based optimization of maltose-binding-protein ligands." PLoS One 10.8 (2015): e0133571.

Ward, Jonathan J., et al. "Prediction and functional analysis of native disorder in proteins from the three kingdoms of life." Journal of molecular biology 337.3 (2004): 635-645.

Van Der Lee, Robin, et al. "Classification of intrinsically disordered regions and proteins." Chemical reviews 114.13 (2014): 6589-6631.

* cited by examiner (SEQ ID NO: 1) WT    G T ▓▓▓▓ H H W Y S E E ▓▓▓▓ A R W Y (SEQ ID NO: 2) Mut 1    G T ▓▓ ▓▓ H H W Y S E E ▓ Y▓ A R W Y (SEQ ID NO: 3) Mut 2    G T ▓▓ H H W Y S E E ▓▓ P A R W Y (SEQ ID NO: 4) Mut 3    G T Y S▓ H H W Y S E E A Y▓ A R W Y (SEQ ID NO: 5) Mut 4    G T G ▓ H H W Y S E E ▓ R ▓ A R W Y

SEQUENCE LISTING

Sequence total quantity: 9
SEQ ID NO: 1              moltype = AA   length = 20
FEATURE                   Location/Qualifiers
REGION                    1..20
                          note = Natural variant of target protein
source                    1..20
                          mol_type = protein
                          organism = synthetic construct
SEQUENCE: 1
GTDEHHHWYS EEGSTVARWY                                            20

SEQ ID NO: 2              moltype = AA   length = 20
FEATURE                   Location/Qualifiers
REGION                    1..20
                          note = Non-natural variant of target protein (Mut 1)
source                    1..20
                          mol_type = protein
                          organism = synthetic construct
SEQUENCE: 2
GTDGHHHWYS EEGWYDARWY                                            20

SEQ ID NO: 3              moltype = AA   length = 20
FEATURE                   Location/Qualifiers
REGION                    1..20
                          note = Non-natural variant of target protein (Mut 2)
source                    1..20
                          mol_type = protein
                          organism = synthetic construct
SEQUENCE: 3
GTTEVHHWYS EEILTPARWY                                            20

SEQ ID NO: 4              moltype = AA   length = 20
FEATURE                   Location/Qualifiers
REGION                    1..20
                          note = Non-natural variant of target protein (Mut 3)
source                    1..20
                          mol_type = protein
                          organism = synthetic construct
SEQUENCE: 4
GTYSAHHWYS EEAMYDARWY                                            20

SEQ ID NO: 5              moltype = AA   length = 20
FEATURE                   Location/Qualifiers
REGION                    1..20
                          note = Non-natural variant of target protein (Mut 4)
source                    1..20
                          mol_type = protein
                          organism = synthetic construct
SEQUENCE: 5
GTGRHHHWYS EEGFRVARWY                                            20

SEQ ID NO: 6              moltype = AA   length = 140
FEATURE                   Location/Qualifiers
REGION                    1..140
                          note = Non-natural variant of target protein
source                    1..140
                          mol_type = protein
                          organism = synthetic construct
SEQUENCE: 6
MDVFMKGLSK AKEGVVAAAE KTKQGVAEAA GKTKEGVLYV GSKTKEGVVH GVATVAEKTK   60
EQVTNVGGAV VTGVTAVAQK TVEGAGSIAA ATGFVKKDQL GKNEEGAPQE GILEDMPVDP  120
DNEAYEMPSE EGYQDYEPEA                                             140

SEQ ID NO: 7              moltype = AA   length = 140
FEATURE                   Location/Qualifiers
REGION                    1..140
                          note = Non-natural variant of target protein
source                    1..140
                          mol_type = protein
                          organism = synthetic construct
SEQUENCE: 7
MDVFMKGLSK AKEGVVAAAE KTKQGVAEAA GKTKEGVLYV GSKTKEGVVK GVATVAEKTK   60
EQVTNVGGAV VTGVTAVAQK TVEGAGSIAA ATGFVKKDQL GKNEEGAPQE GILEDMPVDP  120
DNEAYEMPSE EGYQDYEPEA                                             140

SEQ ID NO: 8              moltype = AA   length = 140
FEATURE                   Location/Qualifiers
REGION                    1..140

-continued

```
                        note = Non-natural variant of target protein
source                  1..140
                        mol_type = protein
                        organism = synthetic construct
SEQUENCE: 8
MDVFMKGLSK AKEGVVAAAE KTKQGVAEAA GKTKEGVLYV GSKTKEGVVE GVATVAEKTK    60
EQVTNVGGAV VTGVTAVAQK TVEGAGSIAA ATGFVKKDQL GKNEEGAPQE GILEDMPVDP   120
DNEAYEMPSE EGYQDYEPEA                                                140

SEQ ID NO: 9            moltype = AA   length = 140
FEATURE                 Location/Qualifiers
REGION                  1..140
                        note = Non-natural variant of target protein
source                  1..140
                        mol_type = protein
                        organism = synthetic construct
SEQUENCE: 9
MDVFMKGLSK AKEGVVAAAE KTKQGVAEAA GKTKEGVLYV GSKTKEGVVY GVATVAEKTK    60
EQVTNVGGAV VTGVTAVAQK TVEGAGSIAA ATGFVKKDQL GKNEEGAPQE GILEDMPVDP   120
DNEAYEMPSE EGYQDYEPEA                                                140
```

SPACIO-TEMPORAL DETERMINATION OF POLYPEPTIDE STRUCTURE

CROSS-REFERENCE

This application is a continuation of U.S. application Ser. No. 18/513,867, filed Nov. 20, 2023, which is a continuation of International Application No. PCT/IB2022/054705, filed May 19, 2022, which claims the benefit of European Application No. 21382464.2, filed May 21, 2021, both of which are incorporated by reference in their entireties.

SEQUENCE LISTING

The instant application contains a Sequence Listing which has been submitted electronically in XML format and is hereby incorporated by reference in its entirety. Said XML copy, created on Mar. 5, 2024, is named 199589-701302-SL and is 13,038 bytes in size.

BACKGROUND

Accurate prediction of polypeptide structures holds the promise of unlocking druggability of proteins implicated in various diseases. While techniques such as X-ray crystallography can be used to elucidate a polypeptide structure, such techniques are hampered in poorly expressed or poorly folded proteins. Accordingly, predicting structures using in silico techniques holds promise in unlocking the therapeutic potential of such proteins.

SUMMARY

Provided herein are methods of in silico polypeptide structure generation, comprising: (a) performing a molecular dynamic (MD) simulation of a polypeptide to generate output data as a function of time, wherein the output data comprises tertiary structure conformation information of the polypeptide; (b) encoding the output data into a function to generate a vector map, wherein the vector map comprises: (i) at least one residue-specific property derived from the MD simulation for an amino acid in the polypeptide; and (ii) at least one pairwise property derived from the MD simulation for at least two amino acids in the polypeptide; and (c) applying a machine learning algorithm to the vector map to generate a predicted polypeptide structure based on the at least one residue-specific property and the at least one pairwise property. In some embodiments, a vector map comprises a D-dimensional array, wherein D is the number of residue-specific properties of (i) and the pairwise properties of (ii). In some embodiments, a machine learning algorithm is an unsupervised algorithm. In some embodiments, a machine learning algorithm is a supervised algorithm. In some embodiments, known structural data can be used as an input prior to performing an MD simulation. Such structural data can be obtained, for example from a static structure generated through X-ray crystallography; or through a dynamic structure generated from, for example, NMR. In some embodiments, a residue-specific property comprises Coulombic energy, Van Der Waals energy, a residue label, a GRAVY score, or any combination thereof. In some embodiments, a pairwise property comprises a Coulombic energy between the at least two amino acid, a Van Der Waals energy between the at least two amino acids, a distance between the at least two amino acids, or any combination thereof. In some embodiments, a function is a continuous time dynamic graph function. In some embodiments, a function is a discrete-time dynamic graph function. In some embodiments, an MD simulation comprises Replica Exchange Molecular Dynamics. In some embodiments, an MD simulation comprises Monte Carlo Dynamics. In some embodiments, an encoding comprises dynamic residue embedding. In some embodiments, the method further comprises generating a second function derived from the function, wherein the second function comprises static protein embedding based on the dynamic residue embedding. In some embodiments, the method further comprises encoding data from a crystal structure into the function. In some embodiments, the method further comprises imputing the predicted structure into a database. In some embodiments, the method further comprises linking the predicted structure to a disease state in the database. In some embodiments, the method further comprises selecting an intervention therapy based on the predicted structure and the disease state. Also disclosed are systems comprising computer-readable memory. In some embodiments, the computer-readable memory comprises instructions for performing the methods of in silico polypeptide structure generation described herein.

Provided herein are methods of generating an epitope structure, comprising: (a) providing a polypeptide sequence; (b) calculating index scores for a plurality of epitope structures in the polypeptide sequence, wherein the index scores are calculated based on at least two of: a structural prominence parameter, a disorder parameter, or a conservation parameter of the epitope, wherein: (i) the conservation parameter is calculated based on conservation of at least two amino acid residues in a multiple sequence alignment comprising the target polypeptide; (ii) the disorder parameter and the structural prominence parameter are derived from a molecular dynamics (MD) simulation of a homology model comprising aggregate structures of homologs of the target polypeptide; and (iii) the index scores are proportional to the structural prominence parameter and the conservation parameter, and are inversely proportional to the disorder parameter; and (c) ranking the index scores to select an epitope structure among the plurality of epitope structures having the highest index score. In some embodiments, the method further comprises generating a paratope structure predicted to specifically bind to the epitope structure. In some embodiments, the method further comprises making a therapeutic comprising the paratope structure. In some embodiments, a therapeutic is a small molecule. In some embodiments, a therapeutic is a polypeptide. In some embodiments, a polypeptide is an antibody. In some embodiments, a polypeptide is a nanobody. In some embodiments, a molecular dynamics simulation is a replicate exchange molecular dynamics simulation. In some embodiments, a structural prominence parameter is determined by a solvent accessible surface area of exposed amino acids in the target polypeptide. In some embodiments, a structural prominence parameter is determined by an atomic volume map of the target polypeptide. In some embodiments, a disorder parameter is determined by a root mean square fluctuation of an alpha carbon in a backbone of the target polypeptide. In some embodiments, a disorder parameter is determined by an N—H bond order in a backbone of the target polypeptide. In some embodiments, the method further comprises generating a free energy surface representation of the target polypeptide based on the homology model, thereby determining represented conformations of the target polypeptide at free energy minima. In some embodiments, the method further comprises bundling the represented conformations based on a magnitude of representation at a given free energy minima. In some embodiments, the method further comprises generating a graph network comprising a graph node and a graph edge prior to calculating the index scores, wherein the graph node comprises an alpha carbon of the polypeptide and the graph edge comprises an interaction between at least two alpha carbon atoms in a backbone of the polypeptide. In some embodiments, the method further comprises applying a clustering algorithm to the graph network. In some embodiments, a clustering algorithm is selected from the group consisting of: K-means clustering, t-distributed stochastic neighbor embedding, and any combination thereof. In some embodiments, the method further comprises applying empirical data to the index scores. In some embodiments, a empirical data comprises an $IC_{50}$ of binding of an antibody to the epitope of the target polynucleotide. In some embodiments, the method further comprises a homology model is a solvated model of the target polypeptide. Also disclosed are systems comprising computer-readable memory. In some embodiments, the computer-readable memory comprises instructions for performing the methods of generating epitope structures described herein.

Also disclosed herein are polypeptides comprising a paratope structure, where the paratope structure is obtained by a method of generating epitope structures described herein.

BRIEF DESCRIPTION OF THE DRAWINGS

Novel features of exemplary embodiments are set forth with particularity in the appended claims. A better understanding of the features and advantages will be obtained by reference to the following detailed description that sets forth illustrative embodiments, in which the principles of the disclosed systems and methods are utilized, and the accompanying drawings of which:

FIG. 7A is a snapshot of the evolution of a pairwise CA graph taken at time t=20 nanoseconds (Timeframe=100) where each node is colored according to the residue type (i.e. the node label), the size of each node is proportional to the related degree and the width of each edge is proportional to the related weight. FIG. 7B is a snapshot of the evolution of a pairwise CA graph taken at time t=50 nanoseconds (Timeframe=500) where each node is colored according to the residue type (i.e the node label), the size of each node is proportional to the related degree and the width of each edge is proportional to the related weight. FIG. 7C schematically summarizes the transition from t=0 to t=20 nanoseconds.

DETAILED DESCRIPTION

Figure 1:
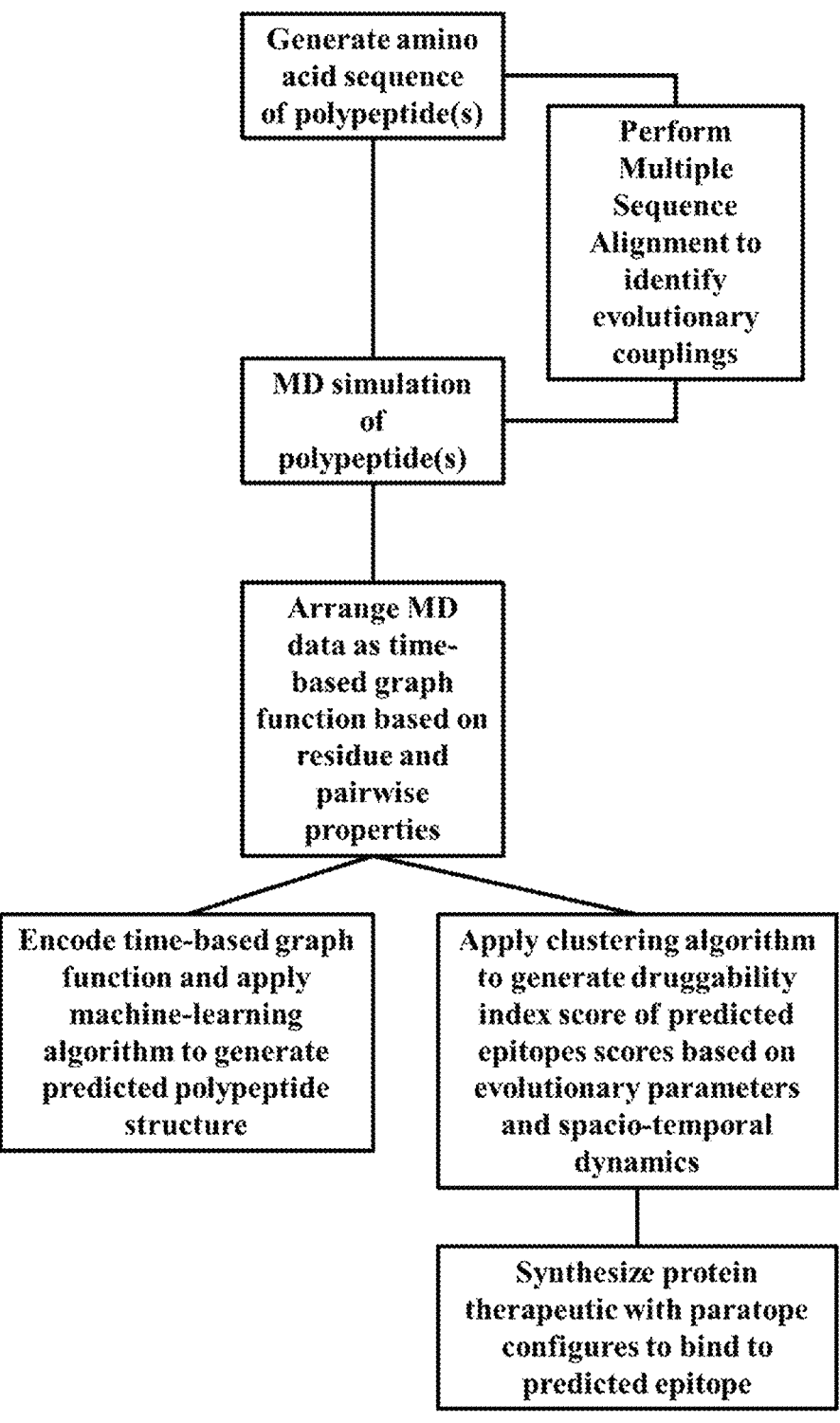
FIG. 1 depicts an exemplary workflow for generating a predicted polypeptide structure and protein therapeutic in silico consistent with embodiments described herein.
Figure 2:
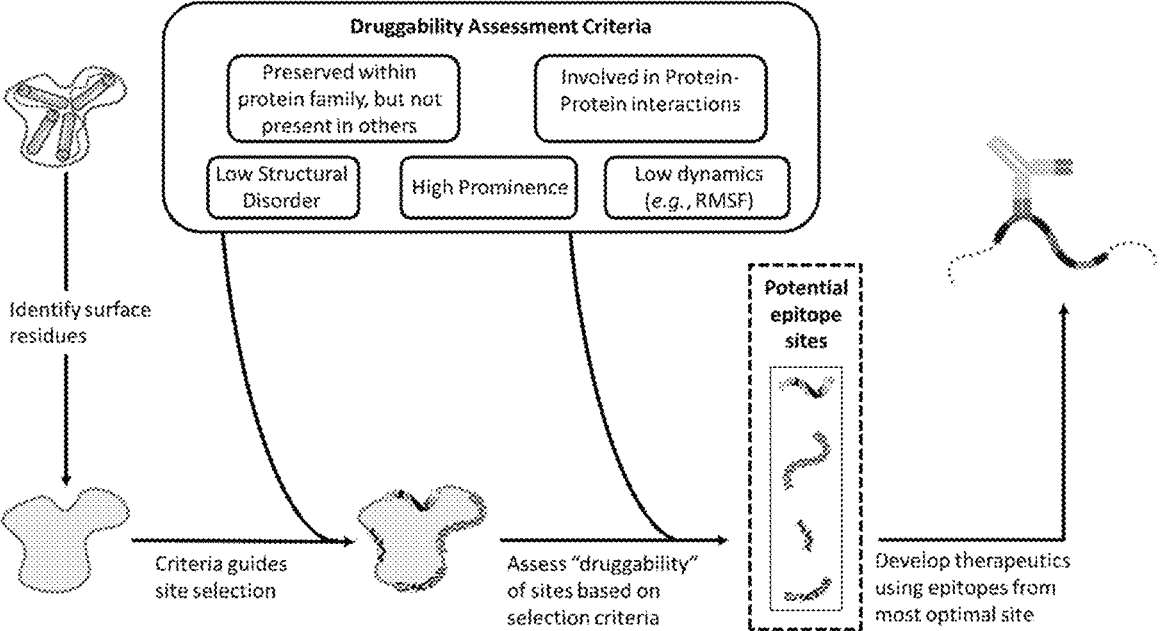
FIG. 2 depicts a schematic assessing druggability of a binding site and generating a therapeutic polypeptide using methods described herein.

Disclosed herein are methods of generating polypeptide structures in silico using big data generated, for example, from molecular dynamics simulations as a function of time. An exemplary workflow for generation of a predicted polypeptide structure using methods described herein is illustrated in FIG. 1. Such data can be processed using machine learning algorithms as described herein to generate a more fulsome predicted polypeptide structure as compared to using existing methods of structural prediction. By allowing a polypeptide structure to vary as a function of time and sample rare conformations along potential energy wells, the predicted structure can more closely match the dynamics that exist in the polypeptide when present in its natural environment. Using this method, binding surfaces and epitopes that are present through dynamic movement of residues separated by significant sequence space can be accurately mapped, which can allow for generation of robust therapeutics that are able to interact with these epitopes. FIG. 2 illustrates a schematic for assessing druggability of predicted epitope sites in a polypeptide and production of protein therapeutics according to methods described herein.

Definitions

The section headings used herein can be for organizational purposes and are not to be construed as limiting the subject matter described. In some cases, the sectional headings may not be constructed as limiting the subject matter described.

As used in the specification and claims, the singular form "a", "an" and "the" include plural references unless the context clearly dictates otherwise. For example, the term "a polypeptide" includes a plurality of polypeptides, including mixtures thereof.

The term "about" or "approximately" as used herein when referring to a measurable value such as an amount or concentration and the like and, unless stated otherwise, is meant to encompass variations of +/−20%, which includes +/−10%, 5%, 1%, 0.5%, or even 0.1% of the specified amount.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure.

Embodiments defined by each of these transition terms are within the scope of this disclosure.

The term "subject," "host," "individual," and "patient" interchangeably refer to animals, typically mammalian animals. Any suitable mammal can be treated by a composition described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal can be a human. A mammal can be any age or at any stage of development (e.g., an adult, teen, child, infant, or a mammal in utero). A mammal can be male or female. A mammal can be a pregnant female. In some embodiments a subject can be a human. In some cases, a human can be more than about: 1 day to about 10 months old, from about 9 months to about 24 months old, from about 1 year to about 8 years old, from about 5 years to about 25 years old, from about 20 years to about 50 years old, from about 1 year old to about 130 years old or from about 30 years to about 100 years old. Humans can be more than about: 1, 2, 5, 10, 20, 30, 40, 50, 60, 70, 80, 90, 100, 110, or 120 years of age. Humans can be less than about: 1, 2, 5, 10, 20, 30, 40, 50, 60, 70, 80, 90, 100, 110, 120 or 130 years of age.

The terms "treating," "treatment," and the like can be used herein to mean obtaining a desired pharmacologic effect, physiologic effect, or any combination thereof. In some instances, a treatment can reverse an adverse effect attributable to the disease or disorder. In some cases, the treatment can stabilize the disease or disorder. In some cases, the treatment can delay progression of the disease or disorder. In some instances, the treatment can cause regression of the disease or disorder. In some instances, the treatment can prevent the occurrence of the disease or disorder. In some embodiments, a treatment's effect can be measured. In some cases, measurements can be compared before and after administration of the composition. For example, a subject can have medical images prior to treatment compared to images after treatment to show cancer regression. In some instances, a subject can have an improved blood test result after treatment compared to a blood test before treatment. In some instances, measurements can be compared to a standard.

The term "protein", "peptide" and "polypeptide" interchangeably and in their broadest sense refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide may contain at least two amino acids and no limitation can be placed on the maximum number of amino acids which may comprise a protein's or peptide's sequence. As used herein the term "amino acid" can refer to natural, unnatural, or synthetic amino acids. Natural, unnatural, or synthetic amino acids can include glycine and both the D and L optical isomers, amino acid analogs and peptidomimetics. As used herein, the term "fusion protein" can refer to a protein comprised of domains from more than one naturally occurring or recombinantly produced protein, where generally each domain serves a different function. In this regard, linker can refer to a protein fragment that can be used to link these domains together—optionally to preserve the conformation of the fused protein domains and/or prevent unfavorable interactions between the fused protein domains which may compromise their respective functions.

"Homology" refers to sequence similarity between two peptides or between two nucleic acid molecules. Homology is determined by comparing a position in each sequence which is aligned for purposes of comparison. When a position in the compared sequence is the same base or amino acid, then the molecules are identical at that position. Sequence homology refers to a % identity of a sequence to a reference sequence. As a practical matter, a homologous sequence has at least 50%, 60%, 70%, 80%, 85%, 90%, 92%, 95%, 96%, 97%, 98% or 99% identity to reference sequence when aligned using known computer programs such the Bestfit program. When using Bestfit or any other sequence alignment program to determine whether a particular sequence is, for instance, 95% identical to a reference sequence, the parameters can be set such that the percentage of identity can be calculated over the full length of the reference sequence and that gaps in sequence homology of up to 5% of the total reference sequence can be allowed. An "unrelated" sequence shares less than 40% identity, or alternatively less than 25% identity, with one of the sequences of the disclosure.

The term "epitope" refers to a portion or structure on a polypeptide that a moiety (e.g. a polypeptide immunoglobulin, antibody, etc.) specifically binds to.

The term "paratope" refers to a structure of a moiety (e.g. a polypeptide immunoglobulin, antibody, etc.) that specifically binds to an epitope.

The term "supervised learning" refers to a deep learning training method in which the machine is provided data from human sources. The term "unsupervised learning" refers to a deep learning training method in which the machine is not provided data from human sources.

The term "semi-supervised learning" refers to a deep learning training method in which the machine is provided a small amount of data from human sources which is then compared to a larger amount of data from other sources available to the machine.

I. Generation of Data from Molecular Dynamics Simulations

Disclosed herein are methods of predicting a polypeptide structure using data input generated from molecular dynamics simulations. Molecular dynamics simulations can be performed in silico to model polypeptide structural conformations and biophysical features. Molecular dynamics simulations can allow for structural dynamics, such that the secondary and tertiary structure of a polypeptide can vary within the timeline of the simulation along allowed conformations. Generally, allowed conformations are those that represent minima along various free energy wells. As such, molecular dynamics simulations can be used to visualize and sample biologically relevant conformations that static structural techniques (e.g. x-ray crystallography) may not sample. Exemplary molecular dynamics simulations for inclusion in methods described herein include, without limitation, Classical Dynamics, Replica Exchange Molecular Dynamics, Meta-Dynamics, Langevin Dynamics and Monte Carlo Dynamics.

Provided herein are methods wherein data generated from molecular dynamic simulations that is relied upon for modeling and predicting polypeptide structures. As described herein, data generated from molecular dynamics simulations is used as an input for machine learning to iterate among allowed and rare structural conformations to generate a more robust and fulsome predicted polypeptide structure. Such data can include residue-specific biophysical properties relevant to a single residue within the molecular dynamics simulation, as well as pairwise properties that relate to a set of biophysical properties relating to interactions between at least two residues within the molecular dynamics simulation. Examples of residue specific biophysical properties generated using molecular dynamics simulations include grand average of hydropathy (GRAVY) scores, a residue identity or label, coulombic energies, Van Der Waals energies, solvent accessible surface area (SASA), side chain order parameter (S2) and the like. Examples of pairwise biophysical properties generated using molecular dynamics simulations include distance between given residues, Coulombic energies, Van Der Waals energies, a fraction of native contacts (Q) and the like.

Figure 3:
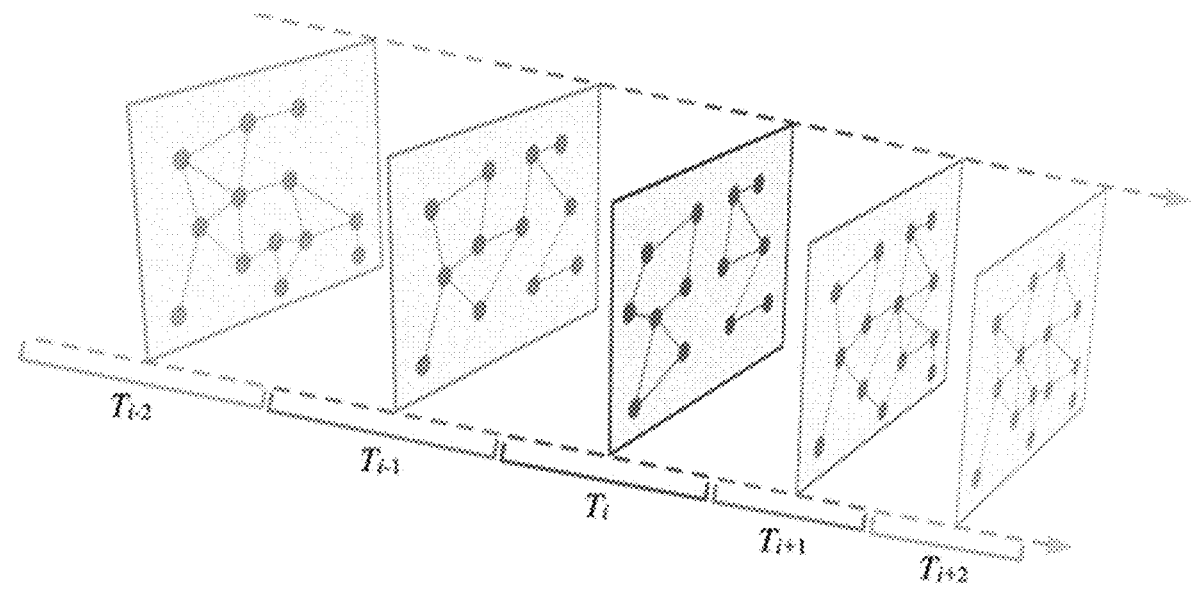
FIG. 3 depicts an illustration of spatio-temporal graphing of individual graph functions as a function of time.

Such properties generated from molecular dynamics can be generated from a given conformation as a function of time. Accordingly, a data set of biophysical properties as a function of time from a set of polypeptide structures can be generated from the molecular dynamics simulations and used as input for machine learning algorithms. This data is arranged into a graph format prior to embedding. Each protein sequence of length L is mapped into undirected graph functions. FIG. 3 illustrates mapping of the individual graph functions as a function of time. Such graph functions can include:

continuous-time dynamic graph $G(V, E_T, \mathcal{T})$ where $V$ represents the set of nodes, $E_T \subseteq V \times V \times \underline{\mathbb{R}}^+$ represents the set of temporal edges between vertices in $V$ and $\mathcal{T}$ is a function that maps each edge to a corresponding timestamp. Each edge $\mathcal{T} e_i=(u, v, t) \in E_T$ is assigned to a unique time $t \in \underline{\mathbb{R}}^+$ where $(u, v)$ represents a couple of residues. This approach takes into account a set of time frames in the molecular dynamics simulation where, each time frame has a unique time t.

discrete-time dynamic graph $\underline{G}$ as a sequence of graphs $G_1, G_2, \ldots, G_T$ from timestamps 1 to T, where each timestamp represents a time frame in the molecular dynamics simulation. Each graph at time t is represented by $G_t=(V_t, E_t)$ where $V_t$ and $E_t$ are the nodes and edges active between the timespan $[t_{i-1}, t_i]$ of the graph respectively.

static graph $G(V, E)$ where $V$ represents the set of nodes and $E$ represents the set of edges.

Each node in the static graph, continuous-time dynamic graph, and discrete time dynamic graph represents a residue while each edge represents the related pairwise residue-residue interaction, obtained from the compression of the information (e.g., arithmetic average) related to each time frame in the molecular dynamics simulation into a single time frame. In each graph function, $\|V\|=L$, i.e. the number of nodes is equal to the sequence length L which can be different for each protein. Data generated from the dynamic graph representation is then encoded to be used as input for machine learning algorithms described herein. In some embodiments, a function $f:V \rightarrow \underline{\mathbb{R}}^D$ that maps each vertex in either the continuous-time dynamic graph $G (V, E_T, \mathcal{T})$ or the discrete-time dynamic graph $G_t(V_t, E_t)$ into a D-dimensional vector is generated, where D is the embedding dimension.

A function can be a conditional log-probability of certain sets of temporal random walks. These are random walks that preserve the time order or the temporal edges, i.e. along a path of such a walk, the timestamp of the consecutive edges are non-decreasing. Additionally, such a function can be represented as a dynamic Skip-gram model trained on evolving random walks where, pre-trained Skip-gram model $SG_{t-1}$ is used as initial weight for the next Skip-gram model $SG_t$. Indeed, other such algorithms can be employed with the methods described herein.

After generation of graph representations as described herein, data is embedded for input into machine learning algorithms as described herein. In some instances, manifold learning techniques, e.g. t-distributed stochastic neighbor embedding (t-SNE), can be used. Embedding as described herein can include dynamic residue embedding and static protein embedding.

In dynamic residue embedding, each protein is mapped/embedded into a dense $2^{nd}$ rank tensor $D^{\mu\nu}$, where $\mu=[0, \ldots, \|V\|]$ is the residue index and $\nu \in [0, \ldots, E_d]$ is the embedding index, where $E_d$ is the dynamic embedding dimension. Hence each residue is embedded into a dense vector $r_i \in \underline{\mathbb{R}}^{E_d}$ for $i=0, \ldots, \|V\|$ and a separate dynamic residue embedding is trained for each continuous-time dynamic graph or continuous-time dynamic graph, representing an element of C, the set of polypeptide structures. Stacking $D^{\mu\nu}$ is derived from each protein sequence in C to generate $D^{\alpha\mu\nu}$ where $\alpha \in [0, \ldots, \|C\|]$ is the protein index. $r_{i_j}$ is the dynamic residue embedding vector where $\underline{j} \in [0, \ldots, \|C\|]$.

In static protein embedding, each protein is mapped/embedded into a dense $1^{st}$ rank tensor $S^\nu$. $\nu \in [0, \ldots, E_s]$ is the embedding index, where $E_s$ is the static embedding dimension, where the data output from dynamic graph embedding is used as an input. Hence each protein is embedded into a dense vector $p \in \underline{\mathbb{R}}^{E_s}$ and a single static protein embedding is trained taking into account every static graph, representing an element of C. Hausdorff distance $d_H(D^{\alpha=x,\mu,\nu}, D^{\alpha=y,\mu,\nu})$, as well as other types of distances such as Frobenius norm that involve the dynamic graph representation, can be used as graph proximity metric $\forall x, y \in [0, \ldots, \|C\|]$. In some cases, the dynamic residue embedding tensors $D^{\alpha=x,\mu,\nu}$ and $D^{\alpha=y,\mu,\nu}$ can be two non-empty subsets of the metric space (R, d) where R represents the set of dynamic residue embedding vectors $r_{i_j} \forall \underline{j} \in [0, \ldots, \|C\|]$ and d is the euclidean distance. Stacking $S^\nu$ coming from each protein sequence in C is then generated to calculate $S^{\alpha\nu}$.

II. Machine Learning

Provided herein are methods wherein tensor representations $D^{\alpha\mu\nu}$ and $S^{\alpha\nu}$ generated from the dynamic and static embedding, respectively, are used as input for machine learning to iteratively generate low energy predicted polypeptide structures. Such machine learning framework can be used to shorten an effective simulation time, execute prediction tasks, and perform design related tasks, such that a more robust and fulsome polypeptide structure can be generated from the limited data obtained from the molecular dynamics simulations. The tensor representations $D^{\alpha\mu\nu}$ and $S^{\alpha\nu}$ generated from the dynamic and static embedding, respectively, allow for accurate prediction of structure beyond the current computational capabilities of molecular dynamics simulations.

In some embodiments, polypeptide structures can be generated using unstructured computation, artificial intelligence or deep learning. In some cases, unstructured computation can be employed such that calculations can be performed iteratively. Further, polypeptide structure calculation can rely on artificial intelligence or deep learning. For example, a method described herein such as random forest can employ deep learning to generate Gini impurity scores that can be used to parse out probes with improved predictive value.

In some embodiments, methods of structural prediction as described herein can employ machine learning and computational intelligence techniques, such as deep neural networks, and combinations of supervised, semi-supervised and unsupervised learning techniques. In some embodiments, methods of structural prediction as described herein employ a supervised algorithm (by way of non-limiting example, linear region, random forest classification, decision tree learning, ensemble learning, bootstrap aggregating, and the like). In some embodiments, methods of structural prediction as described herein employ a non-supervised algorithm (by way of non-limiting example, clustering or association).

In some embodiments, the methods of structural prediction as described herein may be configured to utilize one or more exemplary AI/machine learning techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neutral network technique may be one of, without limitation, feedforward neural network, radial basis function network, recurrent neural network, convolutional network (e.g., U-net) or other suitable network. In some embodiments and, optionally, in combination of any embodiment described above or below, an exemplary implementation of Neural Network may be executed as follows:

a. define Neural Network architecture/model,
    b. transfer the input data to the exemplary neural network model,
    c. train the exemplary model incrementally,
    d. determine the accuracy for a specific number of timesteps,
    e. apply the exemplary trained model to process the newly-received input data,
    f. optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

In some embodiments, the machine learning model for structural prediction processes the biophysical properties encoded in the embeddings described above by applying the parameters of the machine learning model to produce a model output. In some embodiments, the model output may be decoded to generate one or more numerical output values and/or vectors indicative of polypeptide structure.

In some embodiments, the parameters of the machine learning model may be trained based on known polypeptide structures. For example, the biophysical properties may be paired with a target structure and/or measurement to form a training pair, such as historical biophysical properties and an observed structure representing a data point in the relationship between the historical biophysical properties and structure. In some embodiments, the biophysical properties may be provided to the machine learning model, e.g., encoded in the embeddings, to produce data representative of polypeptide structure. In some embodiments, an optimization problem associated with the machine learning model may then compare the polypeptide structure with the known output of a training pair including the historical biophysical properties to determine an error of the polypeptide structure. In some embodiments, the optimization problem may employ a loss function, such as, e.g., Hinge Loss, Multi-class SVM Loss, Cross Entropy Loss, Negative Log Likelihood, or other suitable classification loss function to determine the error of the polypeptide structure based on the known structure.

In some embodiments, the known output may be obtained after the machine learning model produces the prediction, such as in online learning scenarios. In such a scenario, the machine learning model may receive the biophysical properties and generate the model output vector to produce the data representative of polypeptide structure. Subsequently, a user may provide feedback by, e.g., modifying, adjusting, removing, and/or verifying the predicted structure via a suitable feedback mechanism, such as a user interface device (e.g., keyboard, mouse, touch screen, user interface, or other interface mechanism of a user device or any suitable combination thereof). The feedback may be paired with the biophysical properties to form the training pair and the optimization problem may determine an error of the polypeptide structure using the feedback.

In some embodiments, based on the error, the optimization problem may update the parameters of the machine learning model using a suitable training algorithm such as, e.g., backpropagation for a prediction machine learning model. In some embodiments, backpropagation may include any suitable minimization algorithm such as a gradient method of the loss function with respect to the weights of the prediction machine learning model. Examples of suitable gradient methods include, e.g., stochastic gradient descent, batch gradient descent, mini-batch gradient descent, or other suitable gradient descent technique. As a result, the optimization problem may update the parameters of the machine learning model based on the error of predicted structure in order to train the machine learning model to model the correlation between biophysical properties and polypeptide structure in order to produce more accurate prediction of structure based on biophysical properties.

III. Generation of Polypeptide Therapeutics

Figure 4:
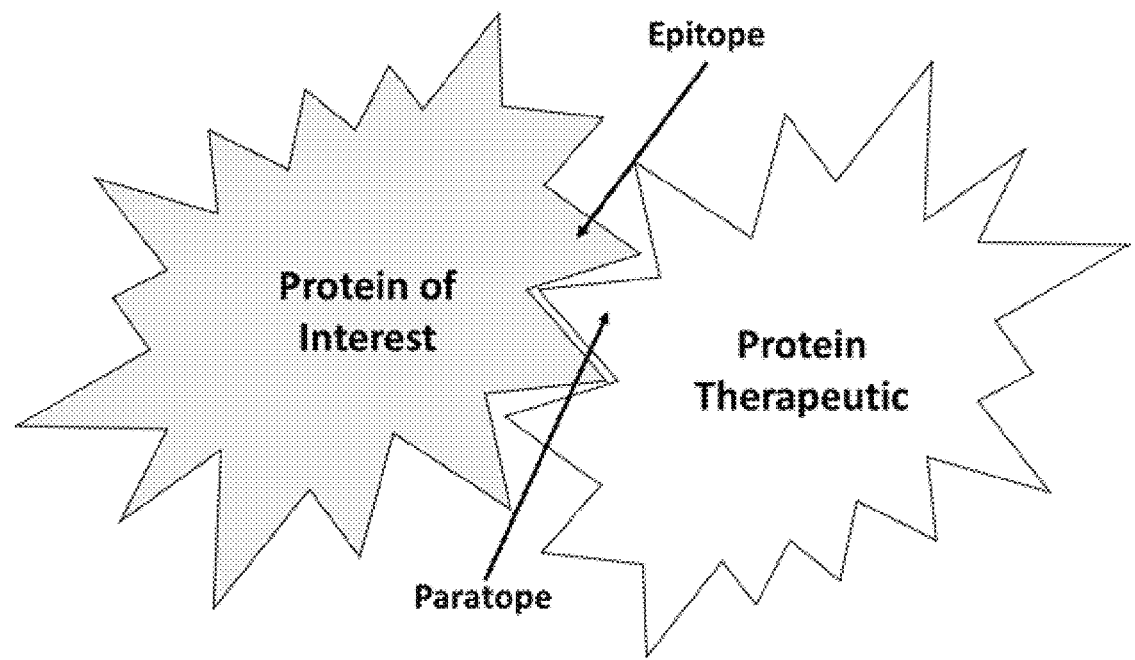
FIG. 4 depicts an interaction between a pair of polypeptides.

As described herein, robust and fulsome polypeptide structures can be predicted using data generated from molecular dynamics simulations using machine learning algorithms as described herein. Knowledge of such structures can be used to effectively and accurately map dynamic surfaces of a polypeptide of interest that is implicated in a disease or condition. By accurately modeling surfaces of polypeptide as a function of time, novel therapeutics can be generated that are able to bind to and interact with an epitope of the polypeptide of interest. Accordingly, such therapeutics can be generated with a paratope structure configured to bind to the epitope and are useful for treatment of diseases or condition. FIG. 4 depicts an illustration of a predicted epitope and paratope structure using methods described herein. Further, by capturing the dynamic structure of polypeptides using methods described herein, rare conformations that are biologically relevant can be predicted which may not be present in static structures such as those generated by x-ray crystallography. Further, iteration using machine learning using the methods described herein allows for robust simulation beyond the capability of molecular dynamics simulations alone, which allows for sampling of rare and short lived (though biologically relevant) conformations that produce epitopes.

Any combination of data can be utilized as described above to generate predicted polypeptide structures using any machine learning algorithm as described above. Further, additional input can be used to provide additional information useful for elucidating biologically relevant epitope conformations. For example, evolutionary covariance among related or homologous polypeptides can be used to determine conservation among residues separated in primary structure and secondary structure by significant distance. Without wishing to be bound by theory, methods described herein utilize evolutionary coupling between a pair of residues as an input to determine whether the pair of residues share a biological function (e.g. are present in the same binding epitope). With such input, dynamic modeling can be performed to determine whether such residues are present in the dynamic structure with minimal entropic penalty. Accordingly, evolutionary coupling and dynamics/disorder parameters are balanced to sample rare yet biologically relevant conformations that give rise to such epitopes.

Where evolutionary couplings are employed, the method described herein comprises generating multiple sequence alignments to determine homology among amino acid sequences. Identity between a reference sequence (query sequence, i.e., a sequence of the disclosure) and a subject sequence, also referred to as a global sequence alignment, can be determined using the FASTDB computer program based on the algorithm of Brutlag et al. (Comp. App. Biosci. 6:237-245 (1990)). In some embodiments, parameters using a FASTDB amino acid alignment, can include: Scoring Scheme=PAM (Percent Accepted Mutations) 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject sequence, whichever can be shorter. According to this embodiment, if the subject sequence is shorter than the query sequence due to N- or C-terminal deletions, not because of internal deletions, a manual correction can be made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are lateral to the N- and C-terminal of the subject sequence, which is not matched/aligned with a corresponding subject residue, as a percent of the total bases of the query sequence. A determination of whether a residue is matched/aligned can be determined by results of the FASTDB sequence alignment. This percentage is then subtracted from the percent identity, calculated by the FASTDB program using the specified parameters, to arrive at a final percent identity score. This final percent identity score can be used for the purposes of this embodiment. In some cases, only residues to the N- and C-termini of the subject sequence, which is not matched/aligned with the query sequence, can be considered for the purposes of manually adjusting the percent identity score. That is, only query residue positions outside the farthest N- and C-terminal residues of the subject sequence may be considered for this manual correction. For example, a 90-residue subject sequence can be aligned with a 100-residue query sequence to determine percent identity. The deletion occurs at the N-terminus of the subject sequence, and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% can be subtracted from the percent identity score calculated by the FASTDB program. If the remaining 90 residues were perfectly matched, the final percent identity can be 90%. In another example, a 90-residue subject sequence can be compared with a 100-residue query sequence. This time the deletions can be internal deletions, so there can be no residues at the N- or C-termini of the subject sequence which can be not matched/aligned with the query. In this case, the percent identity calculated by FASTDB can be not manually corrected. Once again, only residue positions outside the N- and C-terminal ends of the subject sequence, as displayed in the FASTDB alignment, which can be not matched/aligned with the query sequence can be manually corrected for.

In some instances, a known structure can be utilized in conjunction with a sequence as an input for methods described herein. For example, a structure deposited in a protein structure database can be accessed and used as an input for determining novel epitopes. In some instances, empirical structural data can be used as an input. For example a static structure of a target polypeptide obtained by X-ray crystallography can be used an input. Further, a dynamic structure obtained using techniques such as circular dichroism or NMR (e.g. 2D NMR, 3D NMR, solid-state NMR, and the like) can be used as an input.

An exemplary workflow of predicting an epitope structure follows below.

A protein sequence (or a list) is fed into the algorithm.

A multiple sequence alignment (MSA) is performed in order to evaluate evolutionary couplings (EC) between pairs of amino acid residues in the analyzed sequence. An evolutionary coupling reports on a probability that an arbitrary pair of amino acid residues in a given sequence evolved in a coupled fashion and thus is of evolutionary significance and likely has a biological role.

A protein homology 3D model (or models from protein sequence list) that resembles X-ray crystallography or NMR structure is computed.

A solvated 3D model of a protein (using SPC or TIP3 water models) is generated and the remaining, non-neutralized charges get neutralized by an addition of monovalent positive (Na+) and negative (CL−) ions, so that the net charge of a simulated system (the sum of all charges) is equal to zero.

The solvated system is subjected to Replica Exchange Molecular Dynamics (REMD) simulation in which:

a. An arbitrary number of simulation replicas (>2) is initiated. The number itself depends on the system size and scales up with the number of atoms, e.g., a 25000 atom system may require 25 replicas running for 500 nanoseconds each.

b. Every replica receives a copy of an original force-field assigned to the simulation, for which torsional angle potentials, dihedral potentials and selected non-bonded terms are scaled linearly by a factor proportional to the number of replicas. The first replica in the set receives full forces, whereas the last replica is exposed to a modified forcefield scaled by an effective factor equal to 0.5.

Upon the execution of REMD, a Free Energy Surface (FES) of a configurational protein space is reconstructed, so that the most representative structures belonging to different free energy wells can be identified and bundled together as a 3D protein ensemble.

A newly constructed 3D protein ensemble is a subject to a sub-domain identification procedure, which evaluates geometrical and spatio-temporal suitability of a target protein fragments using the following metrics:

a. Structural disorder of individual protein fragments from:

i. Protein backbone H—N bond order parameters (S2).

ii. Root Mean Square Fluctuations (RMSD) of CA atoms in protein backbone.

b. Structural prominence from:

i. Solvent Accessible Surface (SASA) of exposed amino acids.

ii. Atomic volume map (AVM).

A graph network is constructed, in which every CA atom in the original 3D protein molecule is represented by a node, whereas its interactions with neighboring CA backbone atoms are represented by graph edges. In this representation:

a. graph nodes are assigned:

i. RMSF and S2.

ii. the sum of intra-residue interaction energies computed from REMD protocol.

iii. Combined SASA and AVM.

b. graph edges are assigned:

i. intra-residual interaction energies estimated from REMD protocol.

ii. EC probabilities derived from step 2 of the algorithm.

Graph nodes clustering algorithms are applied to graphs from step 8, so that clusters of amino acid residues that share similar spatio-temporal (dynamics) and structural prominence can be identified and flagged as sub-domains. The clustering algorithms may include:

a. K-means clustering.

b. t-distributed stochastic neighbor embedding (t-SNE)

c. and equivalent.

A composite druggability index (DI) is devised and computed for all clustered classes. The score is a sum of structural prominence from SASA and AVM, evolutionary conservation from EC, divided by a sum of RMSF and an inverse of S2. High score indicates domains that are prominent, exposed to solvent yet undergo small structural transitions throughout their molecular dynamics. Moreover, an addition of EC components allows for prioritization of sites with strongly conserved evolutionary features. Low scores denote domains of poor structural prominence, high dynamics and importantly low evolutionary conservation.

The DI score can be further enhanced by an addition of manually curated data on antibody-epitope interactions, such as $IC_{50}$ binding values. Such data can originate from privately performed experiments or through an automated literature search using Natural Language Processing (NLP) methods.

Provided herein are methods wherein after prediction of an epitope surface using methods described herein, a protein therapeutic is designed in silico to comprise a paratope structure that is configured to bind to and interact with the predicted epitope structure. A protein therapeutic can be synthesized using standard FMOC protein synthesis or other standard peptide synthesis techniques used in the art. Alternatively, some protein therapeutics can be expressed in a microorganism such as *Escherichia coli* from a DNA vector. In such embodiments, a polynucleotide sequence encoding the polypeptide of interest is subcloned into an expression vector for overexpression in the microorganism. Successful subcloning of the polynucleotide sequence can be confirmed by sequencing using commercially readily available methods including, without limitation, capillary sequencing, bisulfite-free sequencing, bisulfite sequencing, TET-assisted bisulfite (TAB) sequencing, ACE-sequencing, high-throughput sequencing, Maxam-Gilbert sequencing, massively parallel signature sequencing, Polony sequencing, 454 pyrosequencing, Sanger sequencing, Illumina sequencing, SOLiD sequencing, Ion Torrent semiconductor sequencing, DNA nanoball sequencing, Heliscope single molecule sequencing, single molecule real time (SMRT) sequencing, nanopore sequencing, shot gun sequencing, RNA sequencing, Enigma sequencing, or any combination thereof.

Such protein therapeutics contain high potency of binding for the predicted epitope based on the robust structural sampling methods provided herein. Accordingly, such therapeutic polypeptides display biologically relevant activity against the protein of interest when administered to the subject.

Further, such protein therapeutics are expected to have high specificity and selectivity against the protein of interest. In some cases, a protein of interest can have a specificity of at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% for the target of interest, as determined for example in an in vitro competitive assay. In some cases, a protein of interest can have a selectivity of at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% for the target of interest among other proteins, as determined for example in an in vitro competitive assay.

A therapeutic peptide as described herein can be delivered at any dose required to achieve a biological outcome (e.g. treatment of a disease or condition in a subject). Given the high degree of specificity and potency for therapeutics generated using methods described herein, the dose of therapeutic needed for achieving a biological outcome is lower than therapeutics generated against the same target using comparable methods (i.e. use of only molecular dynamics, mutagenesis, or static structures).

Systems

Also disclosed herein are systems for performing methods described herein. A system can comprise a computer readable memory storing instructions for performing methods described herein. For example, the computer readable memory can comprise instructions for in silico determination of polypeptide structure as described herein. In some embodiments, the computer readable memory can comprise instructions for epitope determination as described herein.

A system can further comprise computer systems utilizing the computer readable memory. Computer systems can include a processor operatively coupled to the computer readable memory, and can be configured to execute the instructions to perform a method described herein. A computer system can further include user input and output means, such as a keyboard, monitor, and mouse.

A system as described herein can be configured to access a database. For example, a system can be configured to access local or online (e.g. cloud) databases such as protein structure database, protein sequence databases, homology databases, nucleic acid sequence databases, and the like.

Upon execution of a method described herein, a system can further comprise data obtained by executing a method described herein. For example, a system upon execution of a method described herein can comprise druggability index scores for determining novel epitopes. Example 5 herein provides an exemplary output of such data that can be stored on a system after execution of a method described herein. A system can comprise structural information obtained from MD simulations described herein. Further, A system ca comprise empirical structural data such as protein structures obtained from NMR or X-ray crystallography. A system can comprise an optimized polypeptide structure obtained using the in silico methods described herein.

Such systems can include storage means for storing or transferring data obtained by the methods described herein. In some instances, the systems can include means to transmit data obtained by the methods described herein into an external database (e.g. a local database or an online database).

EXAMPLES

For a better understanding of the present disclosure and of its many advantages, the following examples are given by way of illustration and without limiting the scope of this disclosure.

Figure 5:
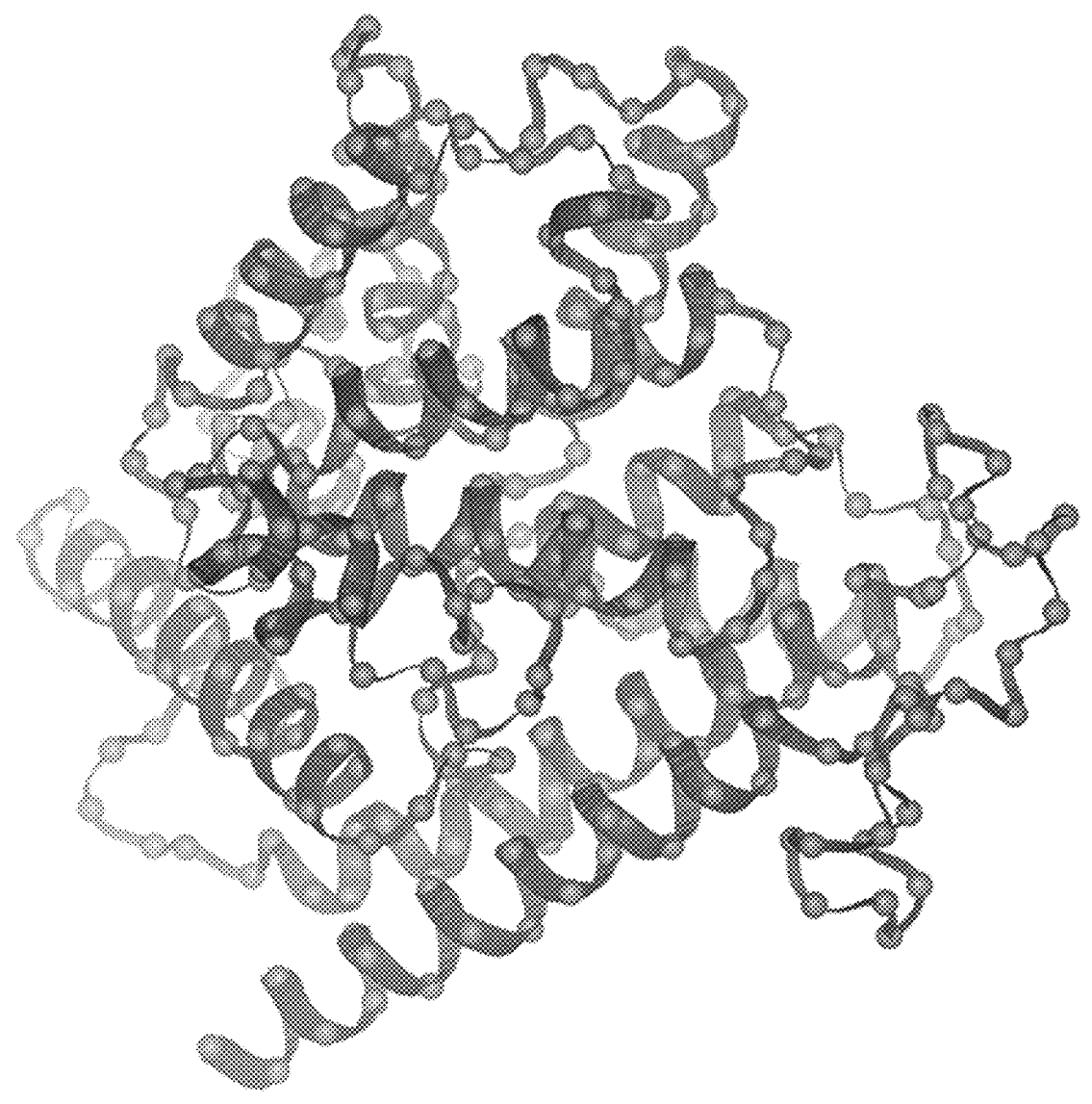
FIG. 5 depicts a cartoon representation of a single polypeptide conformation. Underlying CA atoms in the cartoon representation are represented as spheres, while secondary structures such as alpha helices are present.
Figure 6:
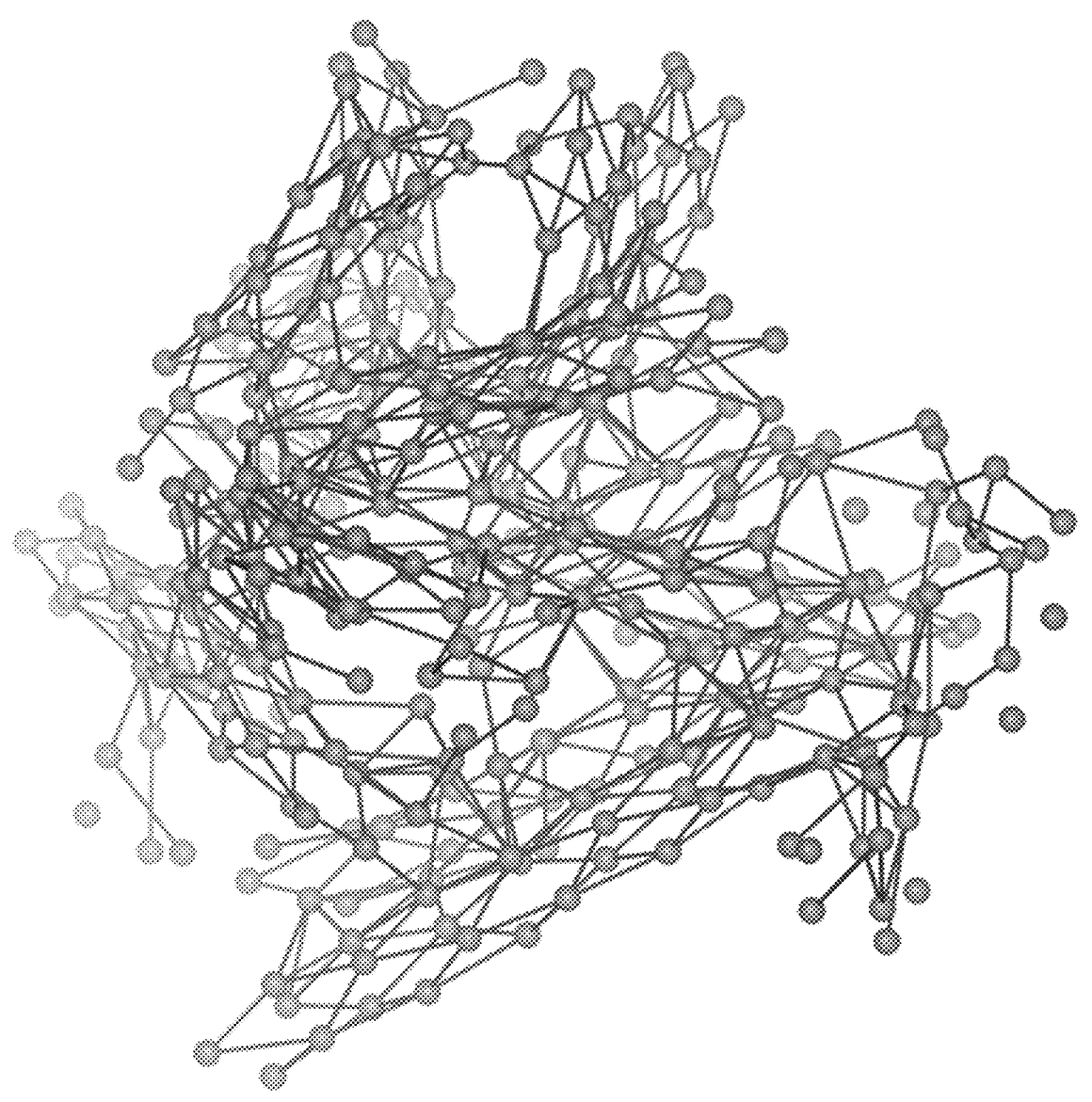
FIG. 6 depicts an exemplary graph representation of a single polypeptide conformation. Nodes in the graph representation represent CA atoms while edges represent interactions between neighboring CA atoms.
Figure 7A:
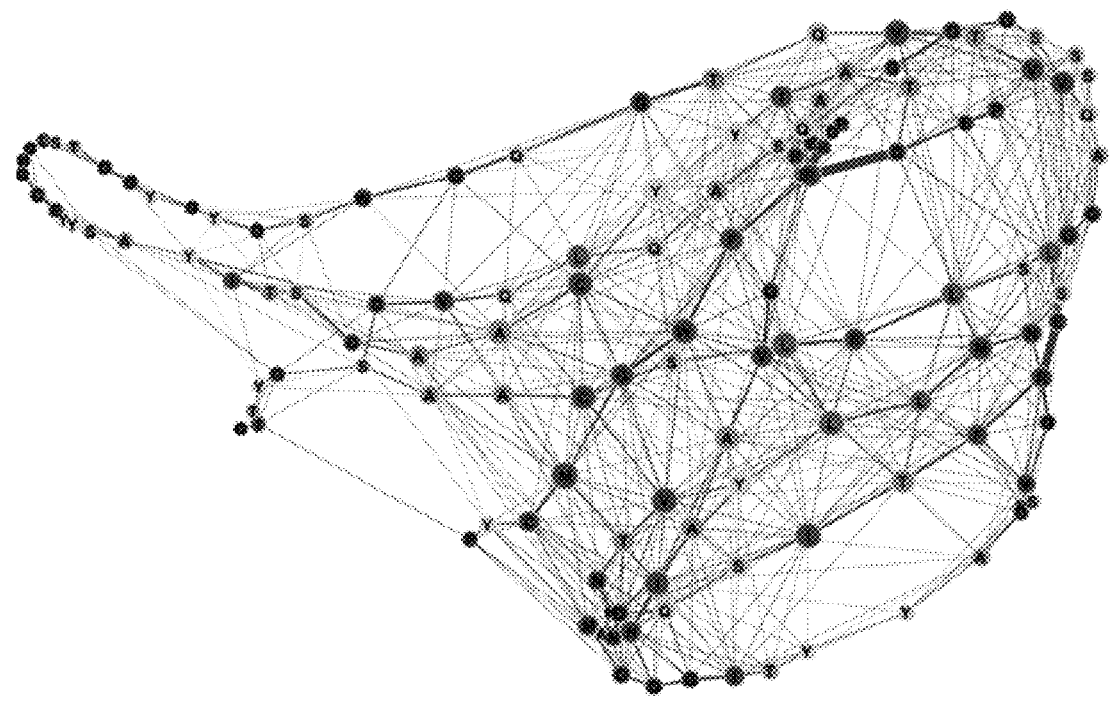
FIGS. 7A, 7B, and 7C illustrate exemplary graph functions as a function of time.
Figure 7B:
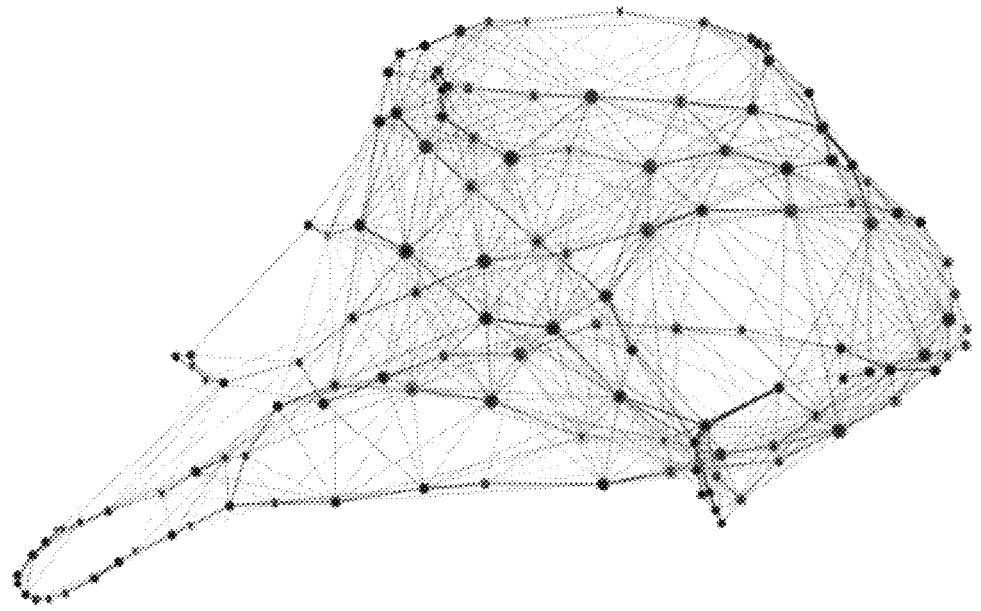
Figure 7C:
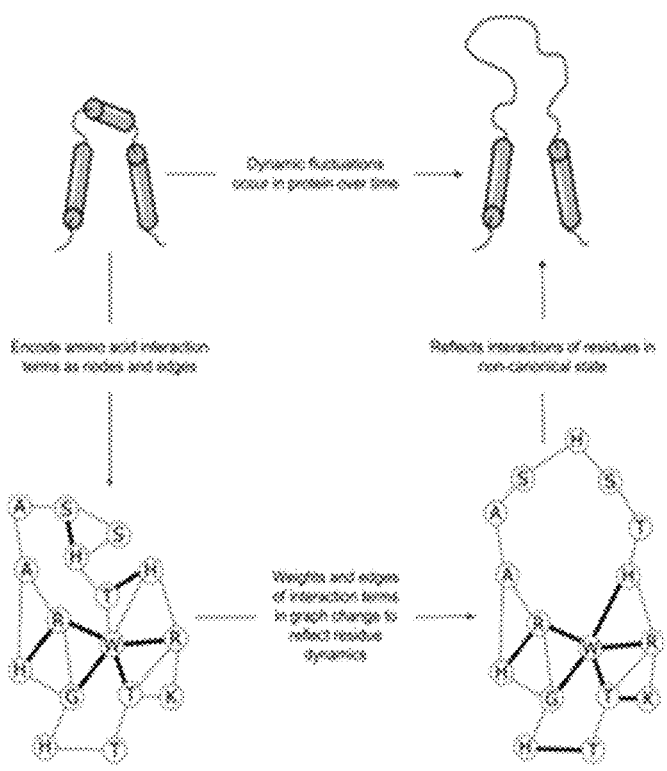

Example 1: Generation of Polypeptide Structures Using Molecular Dynamics Simulations An exemplary polypeptide sequence is input into molecular dynamics simulations to model conformational dynamics of the polypeptide sequence. The model is solvated using TIP3 water models and charges are neutralized using monovalent $Na^+$ and $Cl^-$ ions. FIG. 5 represents a cartoon representation of a polypeptide structure generated using molecular dynamics at a single time point. Each structural conformation at a given time point is arranged into a graph function. FIG. 6 represents an exemplary graph function generated from molecular dynamics for a single conformation at a single timepoint. In this representation, nodes represent individual CA atoms, while edges represent pairwise interactions between residues. FIG. 7A and FIG. 7B illustrate exemplary continuous-time dynamic graphs. FIG. 7A is a snapshot of the evolution of a pairwise CA graph taken at time t=20 nanoseconds (Timeframe=100) where each node is colored according to the residue type (i.e. the node label), the size of each node is proportional to the related degree (i.e. the number of edges or neighbors the node is connected to) and the width of each edge is proportional to the related weight (i.e., the magnitude of the pairwise property). FIG. 7B is a snapshot of the evolution of a pairwise CA graph taken at time t=50 nanoseconds (Timeframe=500) where each node is colored according to the residue type (i.e. the node label), the size of each node is proportional to the related degree and the width of each edge is proportional to the related weight. FIG. 7C schematically summarizes the transition from t=0 to t=20 nanoseconds.

Example 2: Encoding of Graph Function for Machine-Learning Implementation

Data generated from the molecular dynamics simulation performed in Example 1 and converted into graph format are encoded into a vector table for implementation of machine learning algorithms. A continuous-time dynamic graph function $G(V, E_T, \mathcal{T})$ is converted into a D-dimensional vector table, where the number of columns of the table correspond to the properties encoded by the graph function (e.g. Coulombic energy, Van Der Waals energy, GRAVY score, and the like). Table 1 below provides an exemplary vector table generated from a dynamic graph representation representing 6 embedded properties for given amino acid residues.

TABLE 1

| | Exemplary 6-dimensional vector table | | | | | | |
|---|---|---|---|---|---|---|---|
| sequence | embedding_dim_0 | embedding_dim_1 | embedding_dim_2 | embedding_dim_3 | embedding_dim_4 | embedding_dim_5 | embedding_dim_6 |
| D | 0.161965 | 0.064522 | 0.107408 | 0.150810 | 0.081358 | −0.430359 | −0.346224 |
| V | 0.162718 | 0.059577 | 0.107838 | 0.120038 | 0.084629 | −0.446009 | −0.331213 |
| Q | 0.148936 | 0.075921 | 0.107600 | 0.145125 | 0.089531 | −0.424592 | −0.343391 |
| L | 0.151750 | 0.084170 | 0.104289 | 0.148126 | 0.076720 | −0.414987 | −0.345906 |
| Q | 0.182199 | 0.067535 | 0.123472 | 0.136301 | 0.097104 | −0.429192 | −0.335852 |
| . . . | . . . | . . . | . . . | . . . | . . . | . . . | . . . |
| V | 0.165638 | 0.067188 | 0.134613 | 0.152751 | 0.092487 | −0.449565 | −0.338548 |
| T | 0.177571 | 0.076495 | 0.107541 | 0.151998 | 0.100930 | −0.431630 | −0.343449 |
| V | 0.166289 | 0.069632 | 0.126272 | 0.145079 | 0.069669 | −0.425023 | −0.326913 |
| S | 0.175973 | 0.056664 | 0.115223 | 0.129454 | 0.076234 | −0.436164 | −0.346367 |
| S | 0.155674 | 0.083142 | 0.097383 | 0.143570 | 0.076646 | −0.459943 | −0.343468 |

Example 3: Optimization of Dynamic Graph
Representation Using Machine Learning

Manifold learning techniques, including t-distributed stochastic neighbor embedding, are applied to the encoded data generated in Example 2 to generate an optimized dynamic graph representation based on the encoded data. Unsupervised learning algorithms are used to generate the dynamic graph representation iteratively to generate a predicted polypeptide structure.

Example 4: Prediction of Epitope Binding Surface

Evolutionary covariance is determined in silico by performing a multiple sequence alignment of the protein homologs. Pairwise conservation of residues are noted and an evolutionary coupling report is calculated for each arbitrary pair of amino acids based on the probability that the two amino acids evolved in a coupled fashion. Replica Exchange Molecular Dynamics Simulations are performed and data from the MD simulation is generated as described in Example 1. Structural disorder parameters are calculated based on RMSD fluctuations of CA atoms in the MD simulation, while structural prominence parameters are calculated based on solvent accessible surface area of exposed amino acids and atomic volume mapping of the polypeptide. Graph functions are generated as described above for Example 2 and are embedded into a vector comprising data from the structural disorder parameters, the structural prominence parameters, and the evolutionary coupling report. Clustering algorithms are performed using machine learning and optimized polypeptide structures are generated as described above in Example 3.

Figure 8:
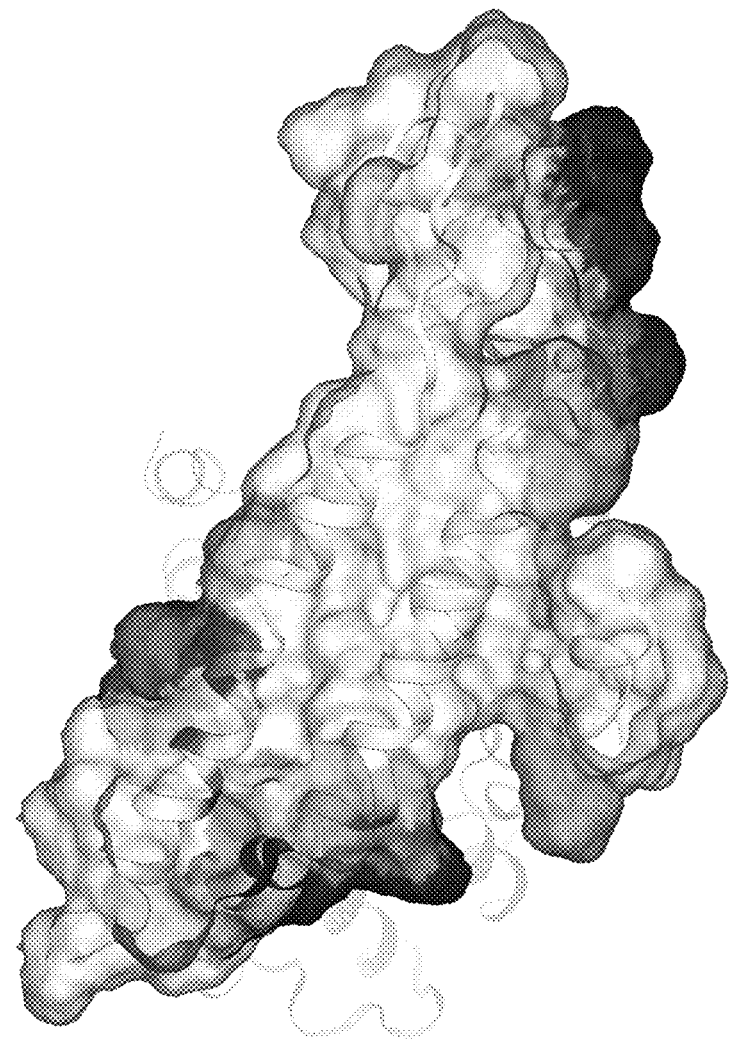
FIG. 8 depicts a surface diagram of an exemplary polypeptide with information generated from the druggability index grafted thereon. Shaded surfaces indicate potential epitopes generated using the druggability index.
Figure 9:
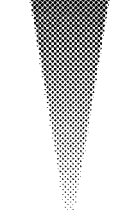
FIG. 9 depicts an exemplary output from the druggability index computation procedure for a number of natural and non-natural variants of the target protein. The shades of gray denote potentially druggable sites.

Clustered residues sharing similar structural disorder parameters, the structural prominence parameters, and the evolutionary coupling are grouped and a composite druggability index score is calculated for the clustered residues. The druggability index score is proportional to the structural prominence parameters and the evolutionary coupling, and inversely proportional to the structural disorder parameters. The druggability index can be mapped onto the predicted structure to identify putative epitopes. FIG. 8 depicts a surface diagram of an exemplary polypeptide with information generated from the druggability index grafted thereon. Shaded surfaces indicate potential epitopes generated using the druggability index. FIG. 9 depicts an exemplary output from the druggability index computation procedure for a number of natural and non-natural variants of the target protein. The shades of gray denote potentially druggable sites.

Example 5—Druggability Index Calculation for
Exemplary Alpha-Synuclein Epitopes

To illustrate the use of disorder parameters for elucidation of novel epitopes, alpha-synuclein variants were compiled for epitope determination. In this study, the effect of mutation at H50 on the druggability of novel epitopes was investigated. H50 is a residue that, when mutated, can result in aggregation of alpha-synuclein. Thus, the ability to design therapeutics targeting novel epitopes of alpha-synuclein variants having mutations at H50 offers profound therapeutic implications.

Structural disorder and structural prominence parameters were calculated based on RMSD fluctuations of CA atoms in an MD simulation of each alpha-synuclein variant as described above for Example 4. Table 2 depicts various parameters calculated from the MD simulation. In the binary disorder prediction, a value of 1 indicates a disorder residue, while 1 value of 0 indicates an ordered residue. In the disordered propensity, the normalized magnitude of the disorder is provided, where a higher value denotes higher likelihood of a given disorder being disordered. A binary druggability index prediction is then calculated, where a value of 1 indicates a disordered epitope-binding residue, a value of 0 indicates a disordered residue other than an epitope-binding residue, and an X indicates a residue that is irrelevant to epitope binding. Finally, a normalized epitope-binding propensity is determined based on the disorder propensity, where a higher value denotes a higher likelihood that a given residue would yield a druggable epitope, while an X indicates a residue that is irrelevant to epitope binding.

As shown in Table 2 below, the disorder parameters can be used to determine an epitope-binding propensity on a residue-by-residue basis for each variant. Of note, residues along the C terminal end having high relative disorder propensity are predicted to have high epitope-binding propensity (values greater than 0.9 are underlined in Table 2) across all variants tested, and thus would be attractive targets for therapeutic targeting. Further, while mutations of H50 itself (residues bolded in Table 2) are believed to play a role in aggregation propensity of alpha-synuclein, the H50Y variant provided herein (SEQ ID NO: 9) displayed a dramatic reduction in disorder along the H50 aggregation surface relative to a variant having the wild-type H50 residue. Thus, the H50 aggregation surface does not appear to be a druggable epitope for variants of alpha-synuclein having the H50Y mutations.

While exemplary embodiments have been shown and described herein, it will be obvious to those skilled in the art that such embodiments are provided by way of example only. Numerous variations, changes, and substitutions will occur to those skilled in the art. It should be understood that various alternatives to the embodiments described herein may be employed. It is intended that the following claims define the scope of the disclosure and that methods and structures within the scope of these claims and their equivalents be covered thereby.

TABLE 2

Calculated druggability index of alpha-synuclein variants

>sp_P37840_SYUA_HUMAN_Alp Residue number

| Residue (SEQ ID NO: 6) | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | M | D | V | F | M | K | G | L | S | K | A | K | E | G | V |
| Binary disorder prediction | 1 | 1 | 1 | 1 | 1 | 1 | 1 | 1 | 1 | 1 | 1 | 1 | 1 | 1 | 1 |
| Disorder propensity | 0.618 | 0.601 | 0.605 | 0.584 | 0.593 | 0.687 | 0.596 | 0.672 | 0.682 | 0.642 | 0.619 | 0.576 | 0.844 | 0.75 | 0.74 |
| Binary druggability index prediction | 0 | 0 | 0 | 0 | 0 | 0 | 0 | 0 | 1 | 0 | 0 | 0 | 0 | 0 | 0 |
| Epitope-binding propensity | 0.485 | 0.451 | 0.451 | 0.464 | 0.464 | 0.486 | 0.49 | 0.498 | 0.501 | 0.457 | 0.457 | 0.457 | 0.455 | 0.454 | 0.453 |

>sp_P37840_SYUA_HUMAN_Alp_1 Residue number

| Residue (SEQ ID NO: 7) | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | M | D | V | F | M | K | G | L | S | K | A | K | E | G | V |
| Binary disorder prediction | 1 | 1 | 1 | 1 | 1 | 1 | 1 | 1 | 1 | 1 | 1 | 1 | 1 | 1 | 1 |
| Disorder propensity | 0.635 | 0.613 | 0.612 | 0.587 | 0.598 | 0.7 | 0.587 | 0.678 | 0.687 | 0.644 | 0.619 | 0.567 | 0.821 | 0.703 | 0.677 |
| Binary druggability index prediction | 0 | 0 | 0 | 0 | 0 | 0 | 0 | 0 | 1 | 0 | 0 | 0 | 0 | 0 | 0 |
| Epitope-binding propensity | 0.49 | 0.451 | 0.451 | 0.464 | 0.464 | 0.486 | 0.49 | 0.498 | 0.501 | 0.457 | 0.457 | 0.457 | 0.455 | 0.449 | 0.447 |

>sp_P37840_SYUA_HUMAN_Alp_2 Residue number

| Residue (SEQ ID NO: 8) | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | M | D | V | F | M | K | G | L | S | K | A | K | E | G | V |
| Binary disorder prediction | 1 | 1 | 1 | 1 | 1 | 1 | 1 | 1 | 1 | 1 | 1 | 1 | 1 | 1 | 1 |
| Disorder propensity | 0.643 | 0.635 | 0.636 | 0.678 | 0.614 | 0.744 | 0.594 | 0.695 | 0.709 | 0.671 | 0.642 | 0.593 | 0.842 | 0.728 | 0.698 |
| Binary druggability index prediction | 0 | 0 | 0 | 0 | 0 | 0 | 0 | 0 | 1 | 0 | 0 | 0 | 0 | 0 | 0 |
| Epitope-binding propensity | 0.49 | 0.457 | 0.457 | 0.469 | 0.464 | 0.497 | 0.49 | 0.498 | 0.507 | 0.457 | 0.457 | 0.457 | 0.455 | 0.449 | 0.441 |

>sp_P37840_SYUA_HUMAN_Alp_3 Residue number

| Residue (SEQ ID NO: 9) | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | M | D | V | F | M | K | G | L | S | K | A | K | E | G | V |
| Binary disorder prediction | 1 | 1 | 1 | 1 | 1 | 1 | 1 | 1 | 1 | 1 | 1 | 1 | 1 | 1 | 1 |
| Disorder propensity | 0.612 | 0.611 | 0.604 | 0.59 | 0.581 | 0.68 | 0.587 | 0.67 | 0.666 | 0.621 | 0.597 | 0.543 | 0.803 | 0.677 | 0.657 |
| Binary druggability index prediction | 0 | 0 | 0 | 0 | 0 | 0 | 0 | 0 | 1 | 0 | 0 | 0 | 0 | 0 | 0 |
| Epitope-binding propensity | 0.485 | 0.451 | 0.451 | 0.464 | 0.464 | 0.486 | 0.49 | 0.498 | 0.501 | 0.457 | 0.457 | 0.457 | 0.455 | 0.448 | 0.447 |

TABLE 2-continued

Calculated druggability index of alpha-synuclein variants

>sp_P37840_SYUA_HUMAN_Alp Residue number

| Residue (SEQ ID NO: 6) | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
| | V | A | A | A | E | K | T | K | Q | G | V | A | E | A | A |
| Binary disorder prediction | 1 | 1 | 1 | 1 | 1 | 1 | 1 | 1 | 1 | 1 | 1 | 1 | 1 | 1 | 1 |
| Disorder propensity | 0.683 | 0.58 | 0.699 | 0.612 | 0.608 | 0.618 | 0.641 | 0.654 | 0.821 | 0.765 | 0.822 | 0.615 | 0.616 | 0.701 | 0.537 |
| Binary druggability index prediction | 0 | 0 | 0 | 0 | 0 | 0 | 0 | 0 | 1 | 0 | 1 | 0 | 1 | 0 | 0 |
| Epitope-binding propensity | 0.447 | 0.442 | 0.468 | 0.475 | 0.485 | 0.497 | 0.497 | 0.495 | 0.502 | 0.494 | 0.509 | 0.487 | 0.501 | 0.487 | 0.487 |

>sp_P37840_SYUA_HUMAN_Alp_1 Residue number

| Residue (SEQ ID NO: 7) | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
| | V | A | A | A | E | K | T | K | Q | G | V | A | E | A | A |
| Binary disorder prediction | 1 | 1 | 1 | 1 | 1 | 1 | 1 | 1 | 1 | 1 | 1 | 1 | 1 | 1 | 1 |
| Disorder propensity | 0.672 | 0.554 | 0.668 | 0.573 | 0.531 | 0.556 | 0.561 | 0.552 | 0.803 | 0.738 | 0.778 | 0.586 | 0.575 | 0.59 | 0.485 |
| Binary druggability index prediction | 0 | 0 | 0 | 0 | 0 | 0 | 0 | 1 | 1 | 0 | 0 | 0 | 0 | 1 | 0 |
| Epitope-binding propensity | 0.447 | 0.442 | 0.468 | 0.475 | 0.485 | 0.497 | 0.497 | 0.509 | 0.511 | 0.48 | 0.5 | 0.481 | 0.471 | 0.501 | 0.48 |

>sp_P37840_SYUA_HUMAN_Alp_2 Residue number

| Residue (SEQ ID NO: 8) | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
| | V | A | A | A | E | K | T | K | Q | G | V | A | E | A | A |
| Binary disorder prediction | 1 | 1 | 1 | 1 | 1 | 1 | 1 | 1 | 1 | 1 | 1 | 1 | 1 | 1 | 1 |
| Disorder propensity | 0.696 | 0.572 | 0.694 | 0.601 | 0.569 | 0.594 | 0.6 | 0.598 | 0.755 | 0.688 | 0.736 | 0.575 | 0.589 | 0.702 | 0.518 |
| Binary druggability index prediction | 0 | 0 | 0 | 0 | 0 | 0 | 0 | 1 | 0 | 0 | 0 | 0 | 0 | 0 | 0 |
| Epitope-binding propensity | 0.447 | 0.442 | 0.47 | 0.475 | 0.485 | 0.497 | 0.492 | 0.509 | 0.491 | 0.48 | 0.489 | 0.483 | 0.48 | 0.494 | 0.475 |

>sp_P37840_SYUA_HUMAN_Alp_3 Residue number

| Residue (SEQ ID NO: 9) | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
| | V | A | A | A | E | K | T | K | Q | G | V | A | E | A | A |
| Binary disorder prediction | 1 | 1 | 1 | 1 | 1 | 1 | 1 | 1 | 1 | 1 | 1 | 1 | 1 | 1 | 1 |
| Disorder propensity | 0.647 | 0.538 | 0.634 | 0.524 | 0.473 | 0.499 | 0.505 | 0.498 | 0.716 | 0.626 | 0.663 | 0.51 | 0.485 | 0.498 | 0.436 |
| Binary druggability index prediction | 0 | 0 | 0 | 0 | 0 | 0 | 0 | 0 | 1 | 0 | 0 | 0 | 0 | 0 | 0 |
| Epitope-binding propensity | 0.447 | 0.442 | 0.468 | 0.463 | 0.466 | 0.481 | 0.481 | 0.481 | 0.508 | 0.485 | 0.48 | 0.483 | 0.478 | 0.485 | 0.469 |

TABLE 2-continued

Calculated druggability index of alpha-synuclein variants

>sp_P37840_SYUA_HUMAN_Alp Residue number

| Residue (SEQ ID NO: 6) | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|
| | G | K | T | K | E | G | V | L | Y | V | G | S | K | T | K |
| Binary disorder prediction | 1 | 1 | 1 | 1 | 1 | 1 | 1 | 1 | 1 | 1 | 1 | 1 | 1 | 1 | 1 |
| Disorder propensity | 0.487 | 0.485 | 0.401 | 0.447 | 0.586 | 0.558 | 0.45 | 0.438 | 0.411 | 0.484 | 0.462 | 0.375 | 0.35 | 0.388 | 0.36 |
| Binary druggability index prediction | 0 | 0 | 0 | 0 | 0 | 0 | 0 | 0 | 0 | 0 | 0 | 0 | 0 | 0 | 0 |
| Epitope-binding propensity | 0.48 | 0.48 | 0.48 | 0.488 | 0.498 | 0.495 | 0.488 | 0.487 | 0.49 | 0.493 | 0.49 | 0.49 | 0.492 | 0.492 | 0.487 |

>sp_P37840_SYUA_HUMAN_Alp_1 Residue number

| Residue (SEQ ID NO: 7) | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|
| | G | K | T | K | E | G | V | L | Y | V | G | S | K | T | K |
| Binary disorder prediction | 1 | 1 | 1 | 1 | 1 | 1 | 1 | 1 | 1 | 1 | 1 | 1 | 1 | 1 | 1 |
| Disorder propensity | 0.441 | 0.446 | 0.381 | 0.412 | 0.509 | 0.509 | 0.356 | 0.392 | 0.4 | 0.423 | 0.386 | 0.371 | 0.354 | 0.406 | 0.38 |
| Binary druggability index prediction | 0 | 0 | 0 | 0 | 0 | 0 | 0 | 0 | 0 | 0 | 0 | 0 | 0 | 0 | 0 |
| Epitope-binding propensity | 0.48 | 0.48 | 0.48 | 0.484 | 0.488 | 0.48 | 0.473 | 0.47 | 0.47 | 0.452 | 0.452 | 0.452 | 0.468 | 0.467 | 0.459 |

>sp_P37840_SYUA_HUMAN_Alp_2 Residue number

| Residue (SEQ ID NO: 8) | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|
| | G | K | T | K | E | G | V | L | Y | V | G | S | K | T | K |
| Binary disorder prediction | 1 | 1 | 1 | 1 | 1 | 1 | 1 | 1 | 1 | 1 | 1 | 0 | 0 | 1 | 1 |
| Disorder propensity | 0.478 | 0.486 | 0.406 | 0.434 | 0.513 | 0.527 | 0.378 | 0.319 | 0.342 | 0.34 | 0.359 | 0.3 | 0.289 | 0.361 | 0.368 |
| Binary druggability index prediction | 0 | 0 | 0 | 0 | 0 | 0 | 0 | 0 | 0 | 0 | 0 | X | X | 0 | 0 |
| Epitope-binding propensity | 0.478 | 0.477 | 0.478 | 0.478 | 0.48 | 0.477 | 0.497 | 0.496 | 0.496 | 0.496 | 0.496 | X | X | 0.496 | 0.496 |

>sp_P37840_SYUA_HUMAN_Alp_3 Residue number

| Residue (SEQ ID NO: 9) | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|
| | G | K | T | K | E | G | V | L | Y | V | G | S | K | T | K |
| Binary disorder prediction | 1 | 1 | 1 | 1 | 1 | 1 | 0 | 0 | 0 | 0 | 0 | 0 | 0 | 0 | 0 |
| Disorder propensity | 0.387 | 0.362 | 0.338 | 0.367 | 0.389 | 0.351 | 0.283 | 0.258 | 0.274 | 0.269 | 0.242 | 0.232 | 0.217 | 0.265 | 0.258 |
| Binary druggability index prediction | 0 | 0 | 0 | 0 | 0 | 0 | X | X | X | X | X | X | X | X | X |
| Epitope-binding propensity | 0.464 | 0.489 | 0.489 | 0.496 | 0.493 | 0.485 | X | X | X | X | X | X | X | X | X |

TABLE 2-continued

Calculated druggability index of alpha-synuclein variants

>sp_P37840_SYUA_HUMAN_Alp Residue number

| | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|
| Residue (SEQ ID NO: 6) | E | G | V | V | H | G | V | A | T | V | A | E | K | T | K |
| Binary disorder prediction | 1 | 1 | 1 | 1 | 1 | 1 | 1 | 1 | 1 | 1 | 1 | 1 | 1 | 1 | 1 |
| Disorder propensity | 0.441 | 0.413 | 0.476 | 0.402 | 0.503 | 0.535 | 0.51 | 0.489 | 0.458 | 0.431 | 0.458 | 0.552 | 0.533 | 0.446 | 0.513 |
| Binary druggability index prediction | 0 | 0 | 0 | 0 | 0 | 0 | 0 | 0 | 0 | 0 | 0 | 0 | 0 | 0 | 0 |
| Epitope-binding propensity | 0.487 | 0.482 | 0.486 | 0.482 | 0.476 | 0.493 | 0.486 | 0.486 | 0.482 | 0.481 | 0.481 | 0.486 | 0.479 | 0.467 | 0.492 |

>sp_P37840_SYUA_HUMAN_Alp_1 Residue number

| | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|
| Residue (SEQ ID NO: 7) | E | G | V | V | K | G | V | A | T | V | A | E | K | T | K |
| Binary disorder prediction | 1 | 1 | 1 | 1 | 1 | 1 | 1 | 1 | 1 | 1 | 1 | 1 | 1 | 1 | 1 |
| Disorder propensity | 0.443 | 0.425 | 0.436 | 0.397 | 0.491 | 0.521 | 0.541 | 0.504 | 0.432 | 0.388 | 0.405 | 0.465 | 0.469 | 0.393 | 0.462 |
| Binary druggability index prediction | 0 | 0 | 0 | 0 | 0 | 0 | 0 | 0 | 0 | 0 | 0 | 0 | 0 | 0 | 0 |
| Epitope-binding propensity | 0.457 | 0.465 | 0.471 | 0.475 | 0.469 | 0.486 | 0.493 | 0.486 | 0.482 | 0.481 | 0.481 | 0.479 | 0.472 | 0.467 | 0.492 |

>sp_P37840_SYUA_HUMAN_Alp_2 Residue number

| | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|
| Residue (SEQ ID NO: 8) | E | G | V | V | E | G | V | A | T | V | A | E | K | T | K |
| Binary disorder prediction | 1 | 1 | 1 | 1 | 1 | 1 | 1 | 1 | 1 | 1 | 1 | 1 | 1 | 1 | 1 |
| Disorder propensity | 0.462 | 0.447 | 0.464 | 0.454 | 0.599 | 0.615 | 0.557 | 0.579 | 0.561 | 0.513 | 0.537 | 0.611 | 0.593 | 0.508 | 0.56 |
| Binary druggability index prediction | 0 | 0 | 0 | 0 | 0 | 0 | 0 | 0 | 0 | 0 | 0 | 0 | 0 | 0 | 0 |
| Epitope-binding propensity | 0.496 | 0.496 | 0.496 | 0.471 | 0.487 | 0.489 | 0.492 | 0.492 | 0.493 | 0.486 | 0.493 | 0.489 | 0.485 | 0.478 | 0.484 |

>sp_P37840_SYUA_HUMAN_Alp_3 Residue number

| | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|
| Residue (SEQ ID NO: 9) | E | G | V | V | Y | G | V | A | T | V | A | E | K | T | K |
| Binary disorder prediction | 0 | 0 | 0 | 0 | 0 | 0 | 0 | 0 | 0 | 0 | 0 | 0 | 1 | 0 | 1 |
| Disorder propensity | 0.292 | 0.281 | 0.245 | 0.234 | 0.254 | 0.263 | 0.263 | 0.258 | 0.267 | 0.224 | 0.25 | 0.294 | 0.309 | 0.287 | 0.347 |
| Binary druggability index prediction | X | X | X | X | X | X | X | X | X | X | X | X | X | X | X |
| Epitope-binding propensity | X | X | X | X | X | X | X | X | X | X | X | X | X | X | X |

TABLE 2-continued

Calculated druggability index of alpha-synuclein variants

>sp_P37840_SYUA_HUMAN_Alp Residue number

| Residue (SEQ ID NO: 6) | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|
| | E | Q | V | T | N | V | G | G | A | V | V | T | G | V | T |
| Binary disorder prediction | 1 | 1 | 1 | 1 | 0 | 0 | 0 | 1 | 0 | 0 | 0 | 0 | 0 | 0 | 0 |
| Disorder propensity | 0.587 | 0.513 | 0.484 | 0.377 | 0.277 | 0.285 | 0.298 | 0.332 | 0.293 | 0.258 | 0.276 | 0.273 | 0.264 | 0.259 | 0.229 |
| Binary druggability index prediction | 1 | 0 | 0 | 0 | X | X | X | 0 | X | X | X | X | X | X | X |
| Epitope-binding propensity | 0.515 | 0.496 | 0.496 | 0.499 | X | X | X | 0.3 | X | X | X | X | X | X | X |

>sp_P37840_SYUA_HUMAN_Alp_1 Residue number

| Residue (SEQ ID NO: 7) | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|
| | E | Q | V | T | N | V | G | G | A | V | V | T | G | V | T |
| Binary disorder prediction | 1 | 1 | 1 | 1 | 0 | 0 | 1 | 1 | 1 | 0 | 0 | 0 | 0 | 0 | 0 |
| Disorder propensity | 0.538 | 0.469 | 0.472 | 0.369 | 0.275 | 0.282 | 0.305 | 0.331 | 0.301 | 0.265 | 0.282 | 0.277 | 0.273 | 0.266 | 0.244 |
| Binary druggability index prediction | 1 | 0 | 0 | 0 | X | X | 0 | 0 | 0 | X | X | X | X | X | X |
| Epitope-binding propensity | 0.515 | 0.493 | 0.496 | 0.496 | X | X | 0.492 | 0.423 | 0.347 | X | X | X | X | X | X |

>sp_P37840_SYUA_HUMAN_Alp_2 Residue number

| Residue (SEQ ID NO: 8) | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|
| | E | Q | V | T | N | V | G | G | A | V | V | T | G | V | T |
| Binary disorder prediction | 1 | 1 | 1 | 1 | 1 | 1 | 1 | 1 | 1 | 0 | 0 | 1 | 0 | 0 | 0 |
| Disorder propensity | 0.627 | 0.558 | 0.546 | 0.429 | 0.324 | 0.329 | 0.348 | 0.373 | 0.339 | 0.279 | 0.299 | 0.302 | 0.299 | 0.291 | 0.269 |
| Binary druggability index prediction | 0 | 0 | 0 | 0 | 0 | 0 | 0 | 0 | 0 | X | X | 0 | X | X | X |
| Epitope-binding propensity | 0.488 | 0.486 | 0.483 | 0.475 | 0.5 | 0.5 | 0.5 | 0.5 | 0.5 | X | X | 0.321 | X | X | X |

>sp_P37840_SYUA_HUMAN_Alp_3 Residue number

| Residue (SEQ ID NO: 9) | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|
| | E | Q | V | T | N | V | G | G | A | V | V | T | G | V | T |
| Binary disorder prediction | 1 | 1 | 1 | 1 | 0 | 0 | 0 | 0 | 0 | 0 | 0 | 0 | 0 | 0 | 0 |
| Disorder propensity | 0.45 | 0.427 | 0.416 | 0.316 | 0.25 | 0.255 | 0.276 | 0.295 | 0.284 | 0.244 | 0.261 | 0.253 | 0.246 | 0.239 | 0.219 |
| Binary druggability index prediction | 0 | 0 | 0 | 0 | X | X | X | X | X | X | X | X | X | X | X |
| Epitope-binding propensity | 0.487 | 0.487 | 0.487 | 0.417 | X | X | X | X | X | X | X | X | X | X | X |

TABLE 2-continued

Calculated druggability index of alpha-synuclein variants

>sp_P37840_SYUA_HUMAN_Alp Residue number

| | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|
| Residue (SEQ ID NO: 6) | A | V | A | Q | K | T | V | E | G | A | G | S | I | A | A |
| Binary disorder prediction | 0 | 0 | 0 | 1 | 1 | 0 | 1 | 1 | 1 | 1 | 1 | 1 | 1 | 1 | 1 |
| Disorder propensity | 0.236 | 0.249 | 0.267 | 0.309 | 0.32 | 0.285 | 0.338 | 0.421 | 0.48 | 0.527 | 0.619 | 0.608 | 0.624 | 0.604 | 0.617 |
| Binary druggability index prediction | X | X | X | 0 | 0 | X | 0 | 0 | 0 | 1 | 1 | 1 | 1 | 1 | 1 |
| Epitope-binding propensity | X | X | X | 0.418 | 0.487 | X | 0.497 | 0.498 | 0.498 | 0.515 | 0.564 | 0.592 | 0.63 | 0.627 | 0.633 |

>sp_P37840_SYUA_HUMAN_Alp_1 Residue number

| | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|
| Residue (SEQ ID NO: 7) | A | V | A | Q | K | T | V | E | G | A | G | S | I | A | A |
| Binary disorder prediction | 0 | 0 | 0 | 1 | 1 | 1 | 1 | 1 | 1 | 1 | 1 | 1 | 1 | 1 | 1 |
| Disorder propensity | 0.255 | 0.267 | 0.283 | 0.329 | 0.347 | 0.31 | 0.376 | 0.451 | 0.51 | 0.542 | 0.618 | 0.605 | 0.622 | 0.59 | 0.599 |
| Binary druggability index prediction | X | X | X | 0 | 0 | 0 | 0 | 0 | 0 | 0 | 1 | 1 | 1 | 1 | 1 |
| Epitope-binding propensity | X | X | X | 0.487 | 0.496 | 0.497 | 0.497 | 0.498 | 0.473 | 0.483 | 0.535 | 0.6 | 0.636 | 0.635 | 0.635 |

>sp_P37840_SYUA_HUMAN_Alp_2 Residue number

| | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|
| Residue (SEQ ID NO: 8) | A | V | A | Q | K | T | V | E | G | A | G | S | I | A | A |
| Binary disorder prediction | 0 | 0 | 0 | 1 | 1 | 1 | 1 | 1 | 1 | 1 | 1 | 1 | 1 | 1 | 1 |
| Disorder propensity | 0.27 | 0.271 | 0.278 | 0.323 | 0.432 | 0.347 | 0.44 | 0.502 | 0.554 | 0.631 | 0.653 | 0.633 | 0.647 | 0.615 | 0.623 |
| Binary druggability index prediction | X | X | X | 0 | 0 | 0 | 0 | 0 | 0 | 0 | 1 | 1 | 1 | 1 | 1 |
| Epitope-binding propensity | X | X | X | 0.487 | 0.496 | 0.497 | 0.497 | 0.498 | 0.477 | 0.483 | 0.548 | 0.6 | 0.636 | 0.635 | 0.635 |

>sp_P37840_SYUA_HUMAN_Alp_3 Residue number

| | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|
| Residue (SEQ ID NO: 9) | A | V | A | Q | K | T | V | E | G | A | G | S | I | A | A |
| Binary disorder prediction | 0 | 0 | 0 | 0 | 0 | 0 | 0 | 1 | 1 | 0 | 1 | 1 | 1 | 1 | 1 |
| Disorder propensity | 0.228 | 0.241 | 0.256 | 0.298 | 0.299 | 0.273 | 0.302 | 0.394 | 0.458 | 0.494 | 0.566 | 0.55 | 0.567 | 0.535 | 0.545 |
| Binary druggability index prediction | X | X | X | X | X | X | 0 | 0 | 0 | 0 | 1 | 1 | 1 | 1 | 1 |
| Epitope-binding propensity | X | X | X | X | X | X | 0.489 | 0.492 | 0.492 | 0.492 | 0.515 | 0.566 | 0.609 | 0.615 | 0.636 |

TABLE 2-continued

Calculated druggability index of alpha-synuclein variants

>sp_P37840_SYUA_HUMAN_Alp Residue number

| Residue (SEQ ID NO: 6) | 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|---|
| | A | T | G | F | V | K | K | D | Q | L | G | K | N | E | E |
| Binary disorder prediction | 1 | 1 | 1 | 1 | 1 | 1 | 1 | 1 | 1 | 1 | 1 | 1 | 1 | 1 | 1 |
| Disorder propensity | 0.689 | 0.745 | 0.791 | 0.751 | 0.752 | 0.751 | 0.884 | 0.82 | 0.788 | 0.906 | 0.879 | 0.833 | 0.791 | 0.795 | 0.83 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.641 | 0.655 | 0.655 | 0.663 | 0.671 | 0.675 | 0.681 | 0.713 | 0.713 | 0.718 | 0.718 | 0.734 | 0.734 | 0.734 | 0.743 |

>sp_P37840_SYUA_HUMAN_Alp_1 Residue number

| Residue (SEQ ID NO: 7) | 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|---|
| | A | T | G | F | V | K | K | D | Q | L | G | K | N | E | E |
| Binary disorder prediction | 1 | 1 | 1 | 1 | 1 | 1 | 1 | 1 | 1 | 1 | 1 | 1 | 1 | 1 | 1 |
| Disorder propensity | 0.65 | 0.721 | 0.765 | 0.722 | 0.728 | 0.714 | 0.792 | 0.795 | 0.756 | 0.878 | 0.838 | 0.787 | 0.762 | 0.771 | 0.813 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.643 | 0.655 | 0.655 | 0.669 | 0.696 | 0.701 | 0.705 | 0.718 | 0.723 | 0.723 | 0.723 | 0.734 | 0.734 | 0.734 | 0.731 |

>sp_P37840_SYUA_HUMAN_Alp_2 Residue number

| Residue (SEQ ID NO: 8) | 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|---|
| | A | T | G | F | V | K | K | D | Q | L | G | K | N | E | E |
| Binary disorder prediction | 1 | 1 | 1 | 1 | 1 | 1 | 1 | 1 | 1 | 1 | 1 | 1 | 1 | 1 | 1 |
| Disorder propensity | 0.671 | 0.737 | 0.78 | 0.74 | 0.747 | 0.73 | 0.812 | 0.818 | 0.779 | 0.889 | 0.851 | 0.805 | 0.777 | 0.787 | 0.823 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.643 | 0.655 | 0.655 | 0.669 | 0.696 | 0.701 | 0.705 | 0.718 | 0.723 | 0.723 | 0.723 | 0.734 | 0.734 | 0.734 | 0.731 |

>sp_P37840_SYUA_HUMAN_Alp_3 Residue number

| Residue (SEQ ID NO: 9) | 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|---|
| | A | T | G | F | V | K | K | D | Q | L | G | K | N | E | E |
| Binary disorder prediction | 1 | 1 | 1 | 1 | 1 | 1 | 1 | 1 | 1 | 1 | 1 | 1 | 1 | 1 | 1 |
| Disorder propensity | 0.603 | 0.689 | 0.739 | 0.697 | 0.708 | 0.703 | 0.782 | 0.793 | 0.753 | 0.876 | 0.816 | 0.766 | 0.748 | 0.748 | 0.803 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.635 | 0.655 | 0.655 | 0.655 | 0.659 | 0.655 | 0.661 | 0.709 | 0.709 | 0.714 | 0.718 | 0.723 | 0.734 | 0.734 | 0.734 |

TABLE 2-continued

Calculated druggability index of alpha-synuclein variants

>sp_P37840_SYUA_HUMAN_Alp Residue number

| Residue (SEQ ID NO: 6) | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|
| | G | A | P | Q | E | G | I | L | E | D | M | P | V | D | P |
| Binary disorder prediction | 1 | 1 | 1 | 1 | 1 | 1 | 1 | 1 | 1 | 1 | 1 | 1 | 1 | 1 | 1 |
| Disorder propensity | 0.831 | 0.84 | 0.839 | 0.818 | 0.844 | 0.847 | 0.851 | 0.853 | 0.892 | 0.813 | 0.794 | 0.865 | 0.856 | 0.847 | 0.838 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.743 | 0.764 | 0.752 | 0.752 | 0.752 | 0.752 | 0.752 | 0.752 | 0.752 | 0.781 | 0.761 | 0.761 | 0.794 | 0.794 | 0.795 |

>sp_P37840_SYUA_HUMAN_Alp_1 Residue number

| Residue (SEQ ID NO: 7) | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|
| | G | A | P | Q | E | G | I | L | E | D | M | P | V | D | P |
| Binary disorder prediction | 1 | 1 | 1 | 1 | 1 | 1 | 1 | 1 | 1 | 1 | 1 | 1 | 1 | 1 | 1 |
| Disorder propensity | 0.854 | 0.852 | 0.852 | 0.824 | 0.852 | 0.853 | 0.851 | 0.848 | 0.893 | 0.842 | 0.804 | 0.875 | 0.862 | 0.861 | 0.85 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.731 | 0.752 | 0.752 | 0.752 | 0.752 | 0.752 | 0.752 | 0.752 | 0.752 | 0.781 | 0.761 | 0.761 | 0.794 | 0.794 | 0.795 |

>sp_P37840_SYUA_HUMAN_Alp_2 Residue number

| Residue (SEQ ID NO: 8) | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|
| | G | A | P | Q | E | G | I | L | E | D | M | P | V | D | P |
| Binary disorder prediction | 1 | 1 | 1 | 1 | 1 | 1 | 1 | 1 | 1 | 1 | 1 | 1 | 1 | 1 | 1 |
| Disorder propensity | 0.86 | 0.857 | 0.854 | 0.825 | 0.852 | 0.854 | 0.851 | 0.848 | 0.893 | 0.843 | 0.805 | 0.876 | 0.862 | 0.863 | 0.851 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.731 | 0.752 | 0.752 | 0.752 | 0.752 | 0.752 | 0.752 | 0.752 | 0.752 | 0.781 | 0.761 | 0.761 | 0.794 | 0.794 | 0.795 |

>sp_P37840_SYUA_HUMAN_Alp_3 Residue number

| Residue (SEQ ID NO: 9) | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|
| | G | A | P | Q | E | G | I | L | E | D | M | P | V | D | P |
| Binary disorder prediction | 1 | 1 | 1 | 1 | 1 | 1 | 1 | 1 | 1 | 1 | 1 | 1 | 1 | 1 | 1 |
| Disorder propensity | 0.857 | 0.852 | 0.852 | 0.825 | 0.853 | 0.853 | 0.852 | 0.849 | 0.893 | 0.843 | 0.805 | 0.876 | 0.863 | 0.862 | 0.851 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.734 | 0.764 | 0.752 | 0.752 | 0.752 | 0.752 | 0.752 | 0.752 | 0.752 | 0.781 | 0.761 | 0.761 | 0.794 | 0.794 | 0.795 |

TABLE 2-continued

Calculated druggability index of alpha-synuclein variants

>sp_P37840_SYUA HUMAN_Alp Residue number

| Residue (SEQ ID NO: 6) | 121 | 122 | 123 | 124 | 125 | 126 | 127 | 128 | 129 | 130 | 131 | 132 | 133 | 134 | 135 |
|---|---|---|---|---|---|---|---|---|---|---|---|---|---|---|---|
| | D | N | E | A | Y | E | M | P | S | E | E | G | Y | Q | D |
| Binary disorder prediction | 1 | 1 | 1 | 1 | 1 | 1 | 1 | 1 | 1 | 1 | 1 | 1 | 1 | 1 | 1 |
| Disorder propensity | 0.804 | 0.847 | 0.881 | 0.842 | 0.899 | 0.874 | 0.852 | 0.892 | 0.881 | 0.889 | 0.895 | 0.918 | 0.919 | 0.92 | 0.872 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.823 | 0.844 | 0.879 | 0.863 | 0.822 | 0.791 | 0.881 | 0.933 | 0.968 | 0.976 | 0.98 | 0.98 | 0.988 | 0.988 | 1 |

>sp_P37840_SYUA_HUMAN_Alp_1 Residue number

| Residue (SEQ ID NO: 7) | 121 | 122 | 123 | 124 | 125 | 126 | 127 | 128 | 129 | 130 | 131 | 132 | 133 | 134 | 135 |
|---|---|---|---|---|---|---|---|---|---|---|---|---|---|---|---|
| | D | N | E | A | Y | E | M | P | S | E | E | G | Y | Q | D |
| Binary disorder prediction | 1 | 1 | 1 | 1 | 1 | 1 | 1 | 1 | 1 | 1 | 1 | 1 | 1 | 1 | 1 |
| Disorder propensity | 0.816 | 0.842 | 0.875 | 0.838 | 0.899 | 0.875 | 0.846 | 0.897 | 0.888 | 0.903 | 0.908 | 0.923 | 0.916 | 0.922 | 0.874 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.823 | 0.844 | 0.879 | 0.863 | 0.822 | 0.791 | 0.881 | 0.933 | 0.968 | 0.976 | 0.98 | 0.98 | 0.988 | 0.988 | 1 |

>sp_P37840_SYUA_HUMAN_Alp_2 Residue number

| Residue (SEQ ID NO: 8) | 121 | 122 | 123 | 124 | 125 | 126 | 127 | 128 | 129 | 130 | 131 | 132 | 133 | 134 | 135 |
|---|---|---|---|---|---|---|---|---|---|---|---|---|---|---|---|
| | D | N | E | A | Y | E | M | P | S | E | E | G | Y | Q | D |
| Binary disorder prediction | 1 | 1 | 1 | 1 | 1 | 1 | 1 | 1 | 1 | 1 | 1 | 1 | 1 | 1 | 1 |
| Disorder propensity | 0.818 | 0.843 | 0.876 | 0.838 | 0.899 | 0.875 | 0.845 | 0.897 | 0.888 | 0.904 | 0.908 | 0.923 | 0.917 | 0.923 | 0.877 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.823 | 0.844 | 0.879 | 0.863 | 0.822 | 0.791 | 0.881 | 0.933 | 0.968 | 0.976 | 0.98 | 0.98 | 0.988 | 0.988 | 1 |

>sp_P37840_SYUA_HUMAN_Alp_3 Residue number

| Residue (SEQ ID NO: 9) | 121 | 122 | 123 | 124 | 125 | 126 | 127 | 128 | 129 | 130 | 131 | 132 | 133 | 134 | 135 |
|---|---|---|---|---|---|---|---|---|---|---|---|---|---|---|---|
| | D | N | E | A | Y | E | M | P | S | E | E | G | Y | Q | D |
| Binary disorder prediction | 1 | 1 | 1 | 1 | 1 | 1 | 1 | 1 | 1 | 1 | 1 | 1 | 1 | 1 | 1 |
| Disorder propensity | 0.816 | 0.845 | 0.875 | 0.839 | 0.898 | 0.872 | 0.845 | 0.895 | 0.996 | 0.09 | 0.905 | 0.921 | 0.915 | 0.922 | 0.873 |
| Binary druggability index prediction | 1 | 1 | 1 | 1 | 1 | 1 | 1 | 1 | 1 | 1 | 1 | 1 | 1 | 1 | 1 |
| Epitope-binding propensity | 0.823 | 0.844 | 0.879 | 0.863 | 0.822 | 0.791 | 0.881 | 0.933 | 0.968 | 0.976 | 0.98 | 0.98 | 0.988 | 0.988 | 1 |

TABLE 2-continued

Calculated druggability index of alpha-synuclein variants

>sp_P37840_SYUA_HUMAN_Alp Residue number

| | 136 | 137 | 138 | 139 | 140 |
|---|---|---|---|---|---|
| Residue (SEQ ID NO: 6) | Y | E | P | E | A |
| Binary disorder prediction | 1 | 1 | 1 | 1 | 1 |
| Disorder propensity | 0.909 | 0.917 | 0.874 | 0.902 | 0.861 |
| Binary druggability index prediction | 1 | 1 | 1 | 1 | 1 |
| Epitope-binding propensity | 1 | 1 | 1 | 1 | 1 |

>sp_P37840_SYUA_HUMAN_Alp_1 Residue number

| | 136 | 137 | 138 | 139 | 140 |
|---|---|---|---|---|---|
| Residue (SEQ ID NO: 7) | Y | E | P | E | A |
| Binary disorder prediction | 1 | 1 | 1 | 1 | 1 |
| Disorder propensity | 0.908 | 0.92 | 0.879 | 0.903 | 0.861 |
| Binary druggability index prediction | 1 | 1 | 1 | 1 | 1 |
| Epitope-binding propensity | 1 | 1 | 1 | 1 | 1 |

>sp_P37840_SYUA_HUMAN_Alp_2 Residue number

| | 136 | 137 | 138 | 139 | 140 |
|---|---|---|---|---|---|
| Residue (SEQ ID NO: 8) | Y | E | P | E | A |
| Binary disorder prediction | 1 | 1 | 1 | 1 | 1 |
| Disorder propensity | 0.909 | 0.921 | 0.88 | 0.904 | 0.862 |
| Binary druggability index prediction | 1 | 1 | 1 | 1 | 1 |
| Epitope-binding propensity | 1 | 1 | 1 | 1 | 1 |

>sp_P37840_SYUA_HUMAN_Alp_3 Residue number

| | 136 | 137 | 138 | 139 | 140 |
|---|---|---|---|---|---|
| Residue (SEQ ID NO: 9) | Y | E | P | E | A |
| Binary disorder prediction | 1 | 1 | 1 | 1 | 1 |
| Disorder propensity | 0.908 | 0.917 | 0.876 | 0.9 | 0.86 |
| Binary druggability index prediction | 1 | 1 | 1 | 1 | 1 |
| Epitope-binding propensity | 1 | 1 | 1 | 1 | 1 |

What is claimed is:

1. A method of analyzing and ranking epitope structures of a target polypeptide for targeting by a therapeutic, the method comprising:

a. providing a polypeptide sequence of a target polypeptide;

b. computing a protein homology model from the polypeptide sequence;

c. applying a molecular dynamics (MD) simulation to the protein homology model to obtain a 3D protein ensemble of the target polypeptide;

d. constructing a graph network by assigning individual alpha carbon atoms in the 3D protein ensemble as nodes and interactions between neighboring alpha carbon backbone atoms as graph edges;

e. identifying a plurality of epitope structures in the polypeptide sequence using a model that is trained to identify epitope structures from the graph network;

f. calculating index scores for the plurality of epitope structures in the polypeptide sequence, wherein the index scores are calculated based on at least two of: a structural prominence parameter, a disorder parameter, or a conservation parameter of the epitope, wherein:

i. the structural prominence parameter is derived from the 3D protein ensemble;

ii. the disorder parameter is determined by a root mean square fluctuation of an alpha carbon in a backbone of the target polypeptide in the 3D protein ensemble;

iii. the conservation parameter is calculated based on conservation of at least two amino acid residues in a multiple sequence alignment comprising the polypeptide sequence of the target polypeptide; and iv. the index scores are proportional to the structural prominence parameter and the conservation parameter, and are inversely proportional to the disorder parameter; and g. ranking an epitope structure among the plurality of epitope structures having the highest index scores in a ranking of index scores, thereby generating a ranked range of epitope structures of the target polypeptide available for subsequent selection for targeting with the therapeutic;

h. selecting the epitope structure with the highest ranked index score from the ranked range of epitope structures of the target polypeptide for generating a paratope structure;

i. generating the paratope structure for the therapeutic that is predicted to bind to the epitope structure; wherein the therapeutic comprises the paratope structure; and j. making the therapeutic by a process that comprises chemical synthesis or expression in a host cell.

2. The method of claim 1, wherein the therapeutic is a small molecule.

3. The method of claim 1, wherein the therapeutic is a polypeptide.

4. The method of claim 3, wherein the polypeptide is an antibody.

5. The method of claim 3, wherein the polypeptide is a nanobody.

6. The method of claim 1, wherein the MD simulation is a replicate exchange MD simulation.

7. The method of claim 1, wherein the structural prominence parameter is determined by a solvent accessible surface area of exposed amino acids in the target polypeptide.

8. The method of claim 1, wherein the structural prominence parameter is determined by an atomic volume map of the target polypeptide.

9. The method of claim 1, wherein the disorder parameter is determined by a root mean square fluctuation of an alpha carbon in a backbone of the target polypeptide.

10. The method of claim 1, wherein the disorder parameter is determined by an N—H bond order in a backbone of the target polypeptide.

11. The method of claim 1, further comprising generating a free energy surface representation of the target polypeptide based on the 3D protein ensemble, thereby determining represented conformations of the target polypeptide at free energy minima.

12. The method of claim 11, further comprising bundling the represented conformations based on a magnitude of representation at a given free energy minima.

13. The method of claim 1, wherein the model that is trained to identify epitope structures from the graph network applies a clustering algorithm to the graph network.

14. The method of claim 13, wherein the clustering algorithm is selected from the group consisting of: K-means clustering, t-distributed stochastic neighbor embedding, and any combination thereof.

15. The method of claim 1, further comprising applying empirical data to the index scores.

16. The method of claim 15, wherein the empirical data comprises an IC50 of binding of an antibody to the epitope of the target polypeptide.

17. The method of claim 1, wherein the protein homology model is a solvated model.

* * * * *